(12) United States Patent
Raslambekov

(10) Patent No.: US 11,426,260 B1
(45) Date of Patent: Aug. 30, 2022

(54) METHODS AND SYSTEMS FOR DETERMINING AN ORTHODONTIC TREATMENT

(71) Applicant: Oxilio Ltd, Larnaca (CY)

(72) Inventor: Islam Khasanovich Raslambekov, Long Island City, NY (US)

(73) Assignee: OXILIO LTD, Larnaca (CY)

( * ) Notice: Subject to any disclaimer, the term of this patent is extended or adjusted under 35 U.S.C. 154(b) by 0 days.

(21) Appl. No.: 17/667,345

(22) Filed: Feb. 8, 2022

(51) Int. Cl.
*A61C 7/00* (2006.01)
*G16H 30/40* (2018.01)
*G16H 30/20* (2018.01)
*A61C 9/00* (2006.01)

(52) U.S. Cl.
CPC ............ *A61C 7/002* (2013.01); *A61C 9/0046* (2013.01); *G16H 30/20* (2018.01); *G16H 30/40* (2018.01)

(58) Field of Classification Search
CPC ...... A61C 7/002; A61C 9/0046; G16H 30/20; G16H 30/40
See application file for complete search history.

(56) References Cited

U.S. PATENT DOCUMENTS

| | | | |
|---|---|---|---|
| 10,856,954 B1 | 12/2020 | Raslambekov | |
| 10,945,812 B1* | 3/2021 | Raslambekov | ......... G06T 5/002 |
| 10,950,061 B1 | 3/2021 | Raslambekov | |
| 10,993,782 B1 | 5/2021 | Raslambekov | |
| 11,026,767 B1 | 6/2021 | Raslambekov | |
| 11,096,763 B2 | 8/2021 | Akopov et al. | |
| 11,116,606 B1 | 9/2021 | Raslambekov | |
| 11,191,618 B1 | 12/2021 | Raslambekov | |
| 2021/0106403 A1 | 4/2021 | Aptekarev et al. | |
| 2022/0071740 A1* | 3/2022 | Raslambekov | ........ A61C 7/002 |

FOREIGN PATENT DOCUMENTS

WO WO-2017172537 A1 * 10/2017 ............. A61C 7/002

OTHER PUBLICATIONS

Chen et al.,"Orthodontic Treatment Based on Wearable Mirror-Type Oral Prosthetic Tongue Flap without Bracket Correction", Published on Jun. 11, 2021, https://www.ncbi.nlm.nih.gov/pmc/articles/PMC8213460/.
U.S. Appl. No. 17/338,143, filed Jun. 3, 2021.

* cited by examiner

*Primary Examiner* — Brenda C Bernardi
(74) *Attorney, Agent, or Firm* — BCF LLP

(57) ABSTRACT

A method and a system for determining an orthodontic treatment plan are provided. The method comprises: acquiring a 3D point cloud representative of surfaces of a given pair of adjacent teeth of a subject; obtaining an indication of a current orthodontic treatment plan for a subject including data of respective tooth trajectories the given pair of adjacent teeth; determining an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth; determining a respective overlap region between the given pair of adjacent teeth caused by the collision; and causing display of respective overlap regions between the adjacent teeth over an indication of the implementation of the current orthodontic treatment plan.

20 Claims, 13 Drawing Sheets

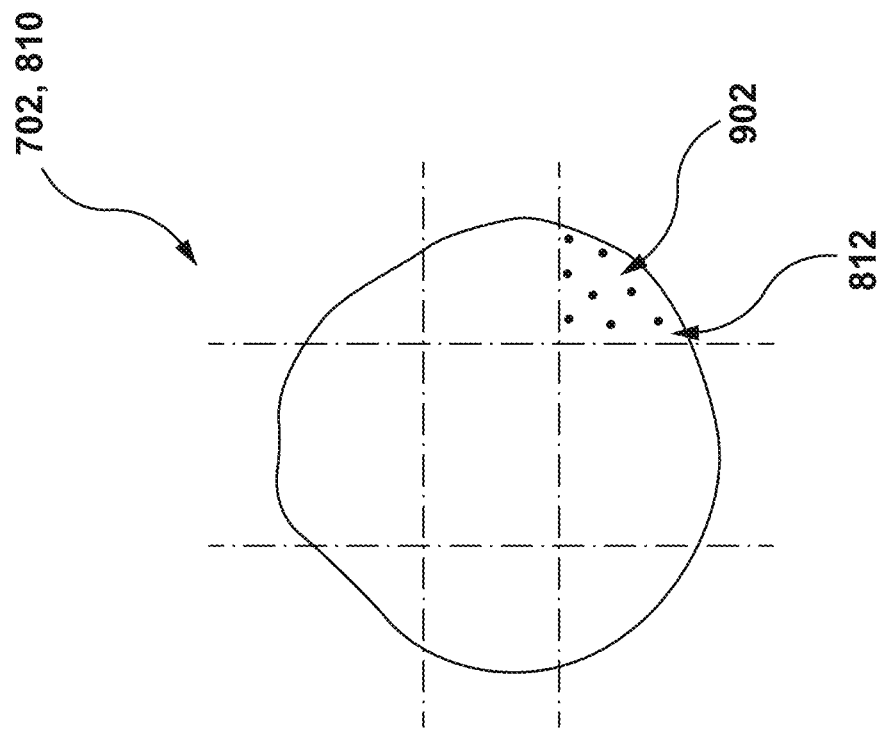
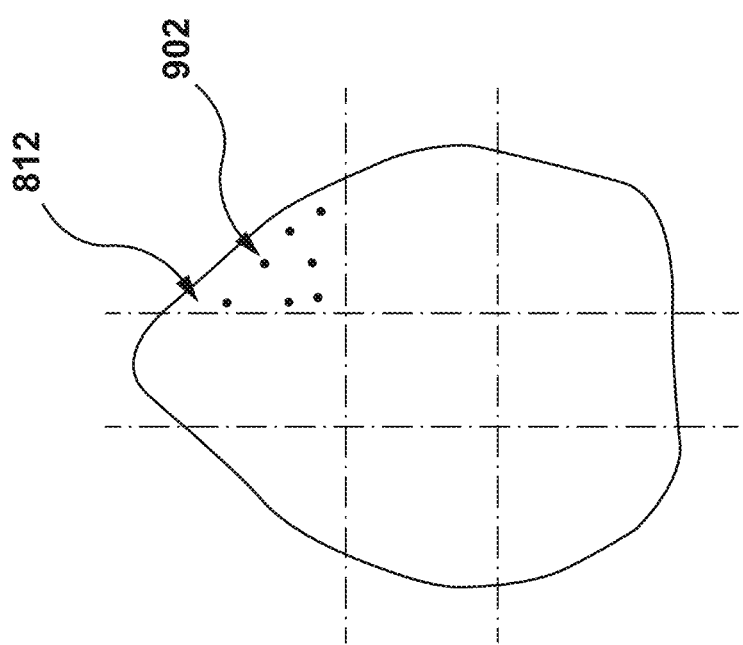
FIG. 9

METHODS AND SYSTEMS FOR DETERMINING AN ORTHODONTIC TREATMENT

FIELD

The present technology relates to systems and methods useful for determining an orthodontic treatment for a subject; and more specifically, although not exclusively, to determining collisions between a pair of adjacent teeth.

BACKGROUND

In orthodontics, planning an orthodontic treatment for a subject may include determining a tooth trajectory for each tooth of a subject's arch form. This may further include modelling tooth movements of a given tooth in the course of the planned orthodontic treatment: from an initial (current) position to a target position of the given tooth, the target position being typically associated with alignment of the given tooth within the subject's arch form. The modelling can be conducted using, for example, a 3D digital model of a subject's arch form, such as a 3D mesh.

Further, once the tooth movements have been modelled, an orthodontic device, such as an aligner (or a set thereof), may be produced and applied to the subject's arch form to exert an external force, over a predetermined treatment interval, onto the given tooth causing it to move, along the so determined tooth trajectory, towards the target position.

However, there are certain contrasting requirements related to the orthodontic treatment: (1) efficiency requirement—minimizing an overall duration of the orthodontic treatment, and (2) safety requirement—ensuring that the planned orthodontic treatment does not cause damage to the subject's teeth or other buccal anatomical structures through collisions or excess applied forces. Also, determining collisions between the subject's teeth using the 3D digital model of the subject's arch form can be a computationally intensive task.

Certain prior art approaches have been proposed to address the technical problem of generating the tooth trajectory for the given tooth considering the above-identified requirements.

U.S. Pat. No. 11,116,606-B1 issued on Sep. 14, 2021, assigned to Arkimos Ltd., and entitled "SYSTEMS AND METHODS FOR DETERMINING A JAW CURVE" discloses a method for determining a jaw curve for orthodontic treatment planning for a patient. The method includes obtaining a tooth and gingiva mesh from image data associated with teeth and surrounding gingiva of the patient, the mesh being representative of a surface of the teeth and the surrounding gingiva; obtaining a tooth contour of each tooth, the tooth contour being defined by a border between a visible portion of each tooth and the surrounding gingiva; determining a tooth contour center of each tooth, the tooth contour center of a given tooth being an average point of the tooth contour of the given tooth; projecting the tooth contour center of each tooth onto a jaw plane; and fitting the tooth contour center of each tooth to a curve to determine the jaw curve.

United States Patent Application Publication No.: 2021/106,403-A1 published on Apr. 15, 2021, assigned to 3d Smile USA Inc, and entitled "APPARATUS AND METHODS FOR ORTHODONTIC TREATMENT PLANNING" discloses an automated process for the design of dental aligners. Specifically, the disclosure relates to a method for generating an orthodontic treatment plan for at least one dental arch of a patient, comprising extracting control points of teeth of the at least one dental arch of the patient from received patient-related data, determining, based on the extracted control points, a target dental arch of the patient, calculating, based on the determined target dental arch of the patient, one or more teeth movement stages, and generating, by processing circuitry and based on the calculated one or more teeth movement stages, the orthodontic treatment plan for the at least one dental arch of the patient.

U.S. Pat. No. 11,096,763-B2 issued on Aug. 24, 2021, assigned Align Technology Inc, and entitled "AUTOMATIC TREATMENT PLANNING" discloses orthodontic and/or dental treatment planning methods and apparatuses. In particular, described therein are methods of generating a plurality of potential treatment plan variations for the concurrent and interactive review of the treatment plan variations. Each variation may be optimized to best address the user's treatment goals, as well as approximating as closely as possible an ideal or target final position. Also described therein are orthodontic and/or dental treatment planning methods and apparatuses that allow a user to form, modify, and select a treatment plan from a plurality of different treatment plans, in real time.

SUMMARY

It is an object of the present technology to ameliorate at least some of the inconveniences present in the prior art.

Developers of the present technology have appreciated that potential collisions between the subject's teeth, using the 3D digital model of the subject's arch form, can be identified in a more efficient fashion during the development and validation of the orthodontic treatment plan for the subject. More specifically, the developers have appreciated that selective application of different approaches to determining a distance between a given pair of adjacent teeth depending on a relative movement therebetween may help reduce a computational burden on a processor. According to at least non-limiting embodiments of the present methods, the value of the so determined distance can be indicative of an occurrence of a collision between the given pair of adjacent teeth.

For example, in a more general case where a movement of a first tooth relative to a second tooth of the given pair includes a combination of rotation and translation, the present methods and systems are directed to determining the distance using a specifically determined distance field associated with the second tooth. The distance field can allow determining respective distances between each vertex representative of the first tooth and that representative of the second tooth. Further, in at least some non-limiting embodiments of the present technology, the distance between the first tooth and the second tooth can be determined as being a minimum one of the respective distances between the vertices thereof.

However, the developers have realized that, if, along a given segment of its tooth trajectory, the first tooth moves only translationally relative to the second tooth, there is no need to consider all the vertices representative of the second tooth for determining the distance thereof from the first tooth. More specifically, in such a case, according to methods and systems described herein, the distance can be determined based on respective distances between each vertex representative of the first tooth and a reference plane specifically determined along a side surface of the second tooth. Further, similarly to the first approach, a minimum respective can be determined as being the distance between the first tooth and the second tooth, the value of which allows to identify the occurrence of the collision between the teeth.

As determining point-to-plane distances is less computationally expensive than determining point-to-point distances using the distance field, the methods and systems described herein allow reducing computational burden on the processor, which further enables to increase the efficiency of the orthodontic treatment plan development.

Additionally, the present methods and systems are directed to using the 3D digital model of the subject's arch form based on 3D point clouds, which allows removing image data representative of edges between mesh elements of conventional 3D mesh models from consideration, and use only vertices thereof for determining the distance between the given pair of adjacent teeth. This may additionally improve the performance of the processor resulting in higher efficiency of determining the orthodontic treatment plan for the subject.

More specifically, in accordance with a first broad aspect of the present technology, there is provided a method of determining an orthodontic treatment plan for a subject. The method is executable by a processor. The method comprises: acquiring, by the processor, a 3D point cloud representative of surfaces of a given pair of adjacent teeth of the subject; obtaining, by the processor, an indication of a current orthodontic treatment plan for the subject, the current orthodontic treatment plan including data of respective tooth trajectories for each one of the given pair of adjacent teeth, the respective tooth trajectories being predetermined, a given tooth trajectory including a respective plurality of segments defining a path of a respective tooth of the given pair of adjacent teeth from a current position to a target position thereof; determining, along a given segment of the respective plurality of segments of at least one of the given pair of adjacent teeth, an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth, such that: in response to the first tooth moving translationally relative to the second tooth: determining, by the processor, based on the 3D point cloud, a reference plane associated with a side surface of the second tooth facing the first tooth; determining, by the processor, respective linear distances between each point representative of the first tooth and the reference plane associated with the second tooth; and in response to determining at least one respective linear distance exceeding a predetermined linear threshold value, determining the occurrence of the collision between the given pair of the adjacent teeth during implementation of the current orthodontic treatment plan; in response to determining that, along the given segment, the first tooth moves rotationally relative to the second tooth: determining, by the processor, a distance field associated with the second tooth of the given pair of adjacent teeth; determining, by the processor, based on the distance field associated with the second tooth, respective arc distances between each point representative of the first tooth and the surface of the second tooth; and in response to determining at least one respective arc distance exceeding a predetermined arc threshold value, determining the occurrence of the collision between the given pair of the adjacent teeth during the implementation of the current orthodontic treatment plan; determining, by the processor, a respective overlap region between the given pair of adjacent teeth caused by the collision therebetween along the given segment; and causing, by the processor, for the given segment of the current orthodontic treatment, display of respective overlap regions between the given pair of adjacent teeth over an indication of the implementation of the current orthodontic treatment plan.

In some implementations of the method, the method further comprises determining the given tooth trajectory for the respective one of the given pair of adjacent teeth based on minimizing, within a predetermined acceptable time range, a time to displace from the current position to the target position.

In some implementations of the method, prior to the determining any one of the respective linear distances and the respective arc distances, the method comprises: generating, by the processor, a voxel grid around the first tooth in the 3D point cloud, a given voxel of the voxel grid includes a respective set of points representative of a surface of the first tooth; and determining, by the processor, in the respective set of points, a respective single point for determining one of a respective linear distance and a respective arc distance between the first tooth and the second tooth.

In some implementations of the method, the determining the respective single point comprises determining, in the respective set of points, an outermost point towards a surface of the second tooth in the 3D point cloud.

In some implementations of the method, the determining the outermost point comprises applying a Bounding Volume Hierarchy algorithm to the given voxel.

In some implementations of the method, the determining the reference plane associated with the side surface of the second tooth comprises determining an average plane from a set of points representative of the side surface of the second tooth within the 3D point cloud.

In some implementations of the method, the determining the reference plane comprises determining a plane extending through at least some outermost points representative of the side surface of the second tooth.

In some implementations of the method, the determining the occurrence of the collision comprises determining one of a minimum respective linear distance and a minimum respective arc distance exceeding a respective one of the predetermined linear threshold value and predetermined arc threshold value.

In some implementations of the method, a given one of the minimum respective linear distance and a minimum respective arc distance are determined using a breadth-first search algorithm.

In some implementations of the method, the method further comprises updating the current orthodontic treatment plan for resolving the collision between the given pair of the adjacent teeth at the given segment.

In some implementations of the method, the updating comprises determining a different tooth trajectory for at least one of the given pair of adjacent teeth.

In some implementations of the method, the updating comprises including, in the current orthodontic treatment plan, a stripping request for stripping material of at least one of the given pair of adjacent teeth within the overlap regions.

In some implementations of the method, the updating comprises including, in the current orthodontic treatment plan, a removal request for removing at least one of the given pair of adjacent teeth.

In some implementations of the method, the method further comprises determining, based on the updated orthodontic treatment plan, a respective configuration of an orthodontic appliance to be applied to subject's teeth over to cause each one of the given pair to displace, along the given segment of the respective plurality of segments, from the current position thereof to the target position thereof without causing the collision therebetween.

In some implementations of the method, the orthodontic appliance is an aligner.

Further, in accordance with a second broad aspect of the present technology, there is provided a method of determining an orthodontic treatment plan for a subject. The method is executable by a processor. The method comprises: acquiring, by the processor, a 3D point cloud representative of surfaces of a given pair of adjacent teeth of the subject;

obtaining, by the processor, an indication of a current orthodontic treatment plan for the subject, the current orthodontic treatment plan including data of respective tooth trajectories for each one of the given pair of adjacent teeth, the respective tooth trajectories being predetermined, a given tooth trajectory including a respective plurality of segments defining a path of a respective tooth of the given pair of adjacent teeth from a current position to a target position thereof; determining, along a given segment of the respective plurality of segments, an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth, such that: in response to the first tooth moving translationally relative to the second tooth, applying, by the processor, a first algorithm to determine a plurality of linear distances between each point representative of the first tooth and the second tooth, in response to determining at least one of the plurality of linear distances exceeding a predetermined linear threshold value, determining the occurrence of the collision between the given pair of the adjacent teeth during implementation of the current orthodontic treatment plan; and in response to determining that, along the given segment, the first tooth moves rotationally relative to the second tooth, applying, by the processor, a second algorithm to determine a plurality of arc distances between each point representative of the first tooth and the second tooth, in response to determining at least one of the plurality of arc distances exceeding a predetermined arc threshold value, determining the occurrence of the collision between the given pair of the adjacent teeth during the implementation of the current orthodontic treatment plan;

determining, by the processor, a respective overlap region between the given pair of adjacent teeth caused by the collision therebetween along each one of the respective plurality of segments; and causing, by the processor, for each one of the respective plurality of segments of the current orthodontic treatment, display of respective overlap regions between the given pair of adjacent teeth over an indication of the implementation of the current orthodontic treatment plan.

Further, in accordance with a third broad aspect of the present technology, there is provided a system for determining an orthodontic treatment plan for a subject. The system comprises: a processor and a non-transitory computer-readable medium storing instructions. The processor, upon executing the instructions, is configured to: acquire a 3D point cloud representative of surfaces of a given pair of adjacent teeth of the subject; obtain an indication of a current orthodontic treatment plan for a subject, the current orthodontic treatment plan including data of respective tooth trajectories for each one of the given pair of adjacent teeth, the respective tooth trajectories being predetermined, a given tooth trajectory including a respective plurality of segments defining a path of a respective tooth of the given pair of adjacent teeth from a current position to a target position thereof; determine, along a given segment of the respective plurality of segments, an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth, such that: in response to the first tooth moving translationally relative to the second tooth: determine, based on the 3D point cloud, a reference plane associated with a side surface of the second tooth facing the first tooth; determine, respective linear distances between each point representative of the first tooth and the reference plane associated with the second tooth; and in response to determining at least one respective linear distance exceeding a predetermined linear threshold value, determine the occurrence of the collision between the given pair of the adjacent teeth during implementation of the current orthodontic treatment plan; in response to determining that, along the given segment, the first tooth moves rotationally relative to the second tooth: determine a distance field associated with the second tooth of the given pair of adjacent teeth; determining, by the pro determine, based on the distance field associated with the second tooth, respective arc distances between each point representative of the first tooth and the surface of the second tooth; and in response to determining at least one respective arc distance exceeding a predetermined arc threshold value, determine the occurrence of the collision between the given pair of the adjacent teeth during the implementation of the current orthodontic treatment plan; determine, a respective overlap region between the given pair of adjacent teeth caused by the collision therebetween along each one of the respective plurality of segments; and cause, for each one of the respective plurality of segments of the current orthodontic treatment, display of respective overlap regions between the given pair of adjacent teeth over an indication of the implementation of the current orthodontic treatment plan.

In some implementations of the system, prior to the determining any one of the respective linear distances and the respective arc distances, the processor is configured to: generate a voxel grid around the first tooth in the 3D point cloud, a given voxel of the voxel grid includes a respective set of points representative of a surface of the first tooth; and determine, in the respective set of points, a respective single point for determining one of a respective linear distance and a respective arc distance between the first tooth and the second tooth.

In some implementations of the system, to determine the respective single point, the processor is configured to determine, in the respective set of points, an outermost point towards a surface of the second tooth in the 3D point cloud.

In some implementations of the system, the processor is further configured to update the current orthodontic treatment plan for resolving the collision between the given pair of the adjacent teeth at each treatment interval.

In accordance with a fourth broad aspect of the present technology, there is provided a method of determining an orthodontic treatment plan for a subject. The method is executable by a processor. The method comprises: acquiring, by the processor, a 3D point cloud representative of surfaces of a given pair of adjacent teeth of the subject; obtaining, by the processor, an indication of a current orthodontic treatment plan for the subject, the current orthodontic treatment plan including data of respective tooth trajectories for each one of the given pair of adjacent teeth, the respective tooth trajectories being predetermined, a given tooth trajectory including a respective plurality of segments defining a path of a respective tooth of the given pair of adjacent teeth from a current position to a target position thereof; determining, along a given segment of the respective plurality of segments of at least one of the given pair of adjacent teeth, an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth, such that: in response to the first tooth moving translationally relative to the second tooth: determining, by the processor, based on the 3D point cloud, a reference plane associated with a side surface of the second tooth facing the first tooth; determining, by the processor, respective linear distances between each point representative of the first tooth and the reference plane associated with the second tooth; and in response to determining at least one respective linear distance exceeding a predetermined linear threshold value, determining the occurrence of the collision between the given pair of the adjacent teeth during implementation of the current orthodontic treatment plan; in response to determining that, along the given segment, the first tooth moves rotationally relative to the second tooth: determining, by the processor, a distance field associated with the second tooth of the given pair of adjacent teeth; determining, by the processor, based on the distance field associated with the second tooth, respective arc distances between each point representative of the first tooth and the surface of the second tooth; and in response to determining at least one respective arc distance exceeding a predetermined arc threshold value, determining the occurrence of the collision between the given pair of the adjacent teeth during the implementation of the current orthodontic treatment plan; determining, by the processor, a respective overlap region between the given pair of adjacent teeth caused by the collision therebetween along the given segment; and based on a configuration of the respective overlap region, updating the current orthodontic treatment plan for resolving the collision between the given pair of the adjacent teeth at the given segment.

In the context of the present specification, the term "orthodontic treatment" is broadly referred to as any type of medical intervention aimed at correcting malocclusions associated with the subject's teeth, including surgical and non-surgical manipulations, such as, but not limited to, using aligners. Further, the orthodontic treatment, as referred to herein, may be determined by a professional practitioner in the field of dentistry (such as an orthodontist, a maxillofacial surgeon, for example), automatically by a specific software, based on respective image data and input parameters associated with the subject, and/or a combination of manual and automatic.

Further, in the context of the present specification, the term "point cloud 3D representation" of an object (such as a subject's arch form) refers to an image thereof, for example, in a three-dimensional space, comprising a plurality of data points, each of which is defined by a respective set of coordinates (x, y, z), thereby representing a surface of the object. In one example, the point cloud 3D representation of the object may be generated by an imaging device such as a 3D laser scanner, where each laser scan corresponds to a respective data point. Further, the laser scans can be merged, or otherwise registered relative to each other, generating the point cloud 3D representation.

In another example, the point cloud 3D representation of the object may be generated by converting a series of 2D images (or a panoramic video) thereof taken from different angles using, for example, specific software.

In yet another example, the point cloud 3D representation may be generated from a respective mesh 3D representation of the object by omitting data of edges defining mesh elements within the respective 3D mesh model and preserving only data of vertices thereof.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 9 depicts lateral and horizontal projections of a respective 3D digital model of a given one of the subject's teeth present in FIG. 1 illustrating a step for determining, by the processor of FIG. 5, points representative of the collision thereof with its neighboring tooth, in accordance with certain non-limiting embodiments of the present technology;

It should be noted that, unless otherwise explicitly specified herein, the drawings are not to scale.

DETAILED DESCRIPTION

Certain aspects and embodiments of the present technology are directed to methods of and systems for planning orthodontic treatment plans including resolving collisions identified described and claimed herein.

More specifically, certain aspects and embodiments of the present technology comprise a computer-implemented method of detecting collisions between adjacent teeth of the subject in a preliminary orthodontic treatment plan therefor, resolving the detected collisions, and thus updating the preliminary orthodontic treatment plan that would not include the collisions.

Additionally, the identifying the collisions may be conducted after the determining the orthodontic treatment, for example, for verification thereof in terms of its safety and/or efficacy. For example, the verification of the determined orthodontic treatment may include modelling effect of the orthodontic appliance onto the subject's teeth.

Certain embodiments of the present technology minimize, reduce or avoid some of the problems noted with the prior art. For example, by implementing certain embodiments of the present technology in respect of determining occurrences of collisions between a given pair of adjacent teeth of the subject, one or more of the following advantages may be obtained: processing fewer points of point cloud 3D representations of the subject's teeth for identifying collisions therebetween, which may allow reducing computational resources consumption on developing orthodontic treatments. Thus, methods and systems provided herein, according to certain non-limiting embodiments of the present technology, allow identifying collisions between the subject's teeth using fewer points of the point cloud 3D representations thereof without compromising accuracy of collision detection, whilst reducing a required computational resource of the processor for devising the orthodontic treatment for the subject.

Orthodontic Treatment

Figure 1:
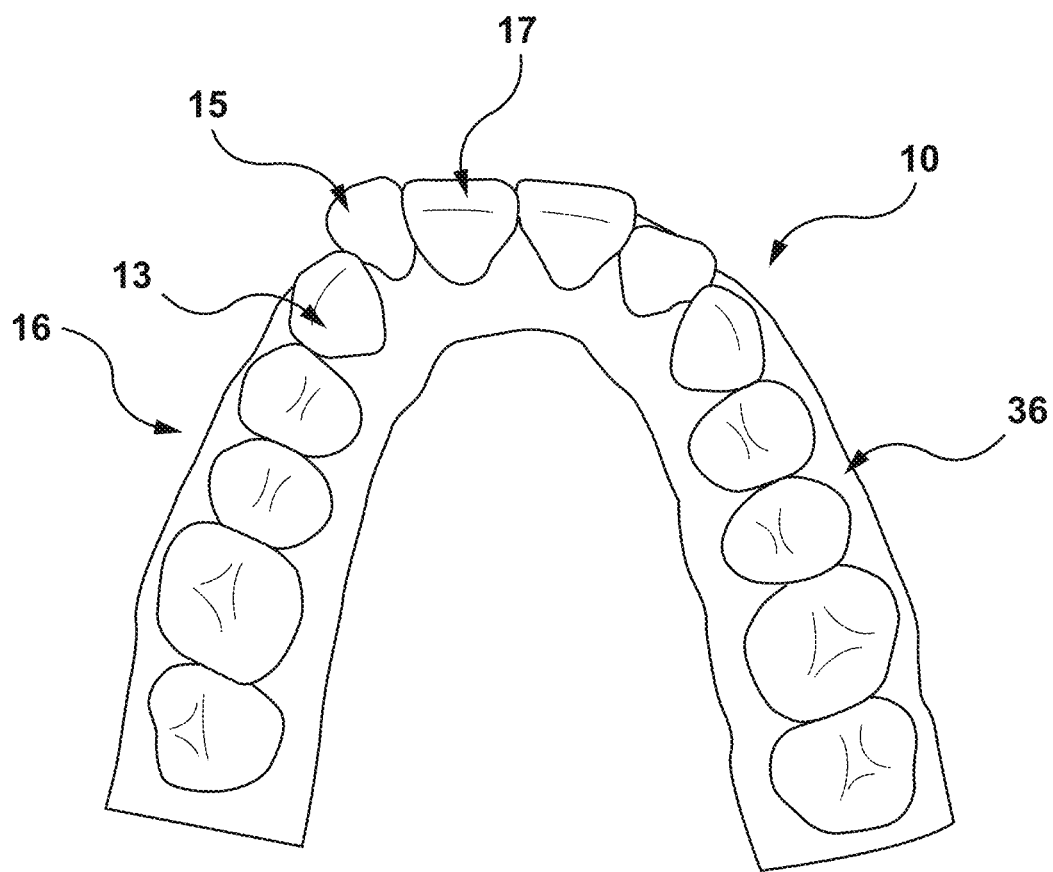
FIG. 1 depicts a bottom view of an upper arch form of a subject depicting examples of malocclusions of some of subject's teeth, in accordance with certain non-limiting embodiments of the present technology.

Referring initially to FIG. 1, there is depicted a bottom view of an upper arch form 10 of the subject, to which certain aspects and non-limiting embodiments of the present technology may be applied.

As it can be appreciated, the upper arch form 10 includes upper teeth 16 and an upper gingiva 36. Further, in the depicted embodiments of FIG. 1, a given tooth 15 is misaligned within the upper teeth 16 as it protrudes outwardly relative to its neighboring teeth, a first adjacent tooth 13 and a second adjacent tooth 17.

Other malocclusions (not depicted) associated with misalignment of the upper teeth 16, according to certain non-limiting embodiments of the present technology, may include, without limitation: crowding of some of the upper teeth 16, excess spacing therebetween, midline shift thereof, and others.

In some non-limiting embodiments of the present technology, for resolving the above-mentioned malocclusions, an orthodontic treatment may be provided to the subject.

In some non-limiting embodiments of the present technology, the orthodontic treatment may comprise applying an orthodontic appliance. Generally speaking, the orthodontic appliance may be configured to exert a respective predetermined force onto at least some of the upper teeth 16—such as those of the upper teeth 16 positioned on the left-hand side before the given tooth 15, such as the first adjacent tooth 13. More specifically, in the depicted embodiments of FIG. 1, the orthodontic appliance may be configured to cause the teeth positioned before the given tooth 15 to move backwards for creating space for the given tooth 15. Further, the orthodontic appliance can be configured to cause the given tooth 15 to move towards an aligned position thereof, that is, inwardly within the so created space between the first adjacent tooth 13 and the second adjacent tooth 17.

In various non-limiting embodiments of the present technology, the orthodontic appliance may comprise orthodontic appliances of different types, shapes, sizes and configurations, such as those including, without limitation, aligners, brackets, multi-strand wires, strips, retainers, and plates.

Figure 2A:
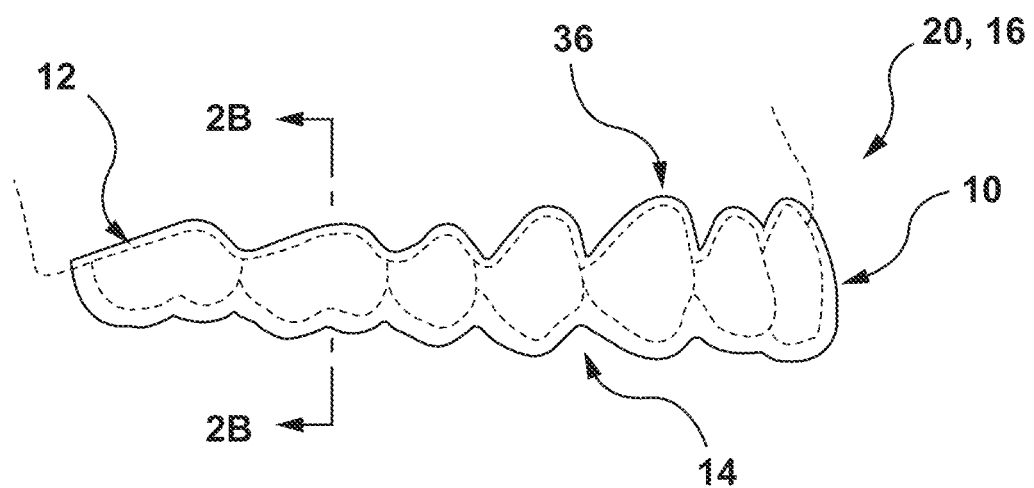
FIGS. 2A and 2B depict side and cross-sectional views, respectively, of a dental appliance applied to the subject's teeth that may be configured to treat the malocclusions of the subject's teeth present in FIG. 1, in accordance with certain non-limiting embodiments of the present technology.
Figure 2B:
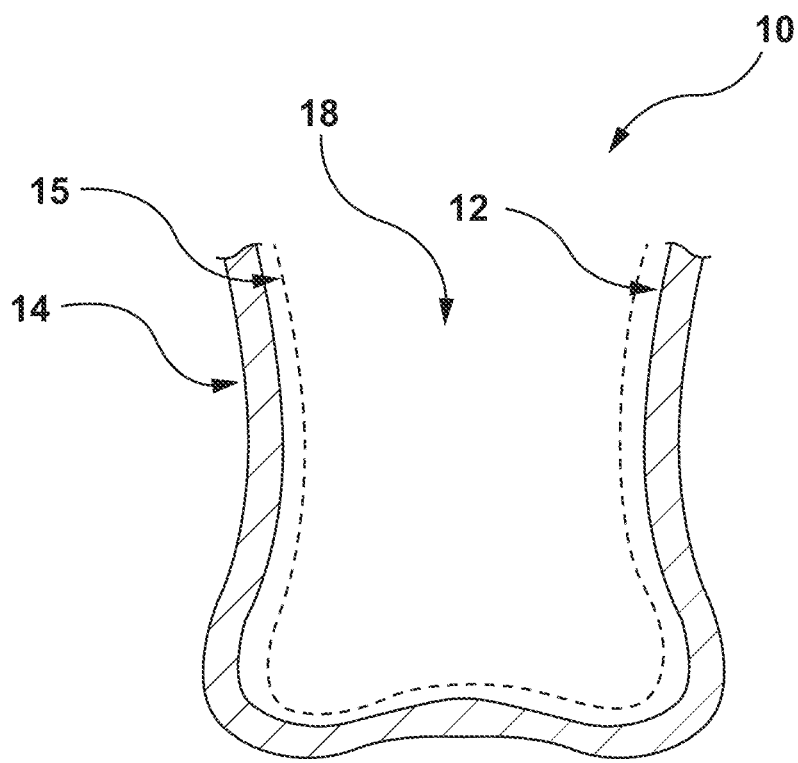

In specific non-limiting embodiments of the present technology, the orthodontic appliance may include at least one aligner. With reference to FIGS. 2A and 2B, there is depicted an aligner 20 applied to at least some of the upper teeth 16, in accordance with certain non-limiting embodiments of the present technology. The aligner 20 comprises an inner surface 12 and an outer surface 14. The inner surface 12 defines a channel 18, which is configured, in some non-limiting embodiments of the present technology, for receiving crown portions of at least some of the upper teeth 16, such as the given tooth 15, the first adjacent tooth 13, and the second adjacent tooth 17. However, in other non-limiting embodiments of the present technology, the channel 18 of the aligner 20 may be configured to receive crown portions of all of the upper teeth 16. At least one edge (also referred to herein as an "open edge") of the channel 18 is shaped for following a gum line (not depicted) along the upper gingiva 36.

It is appreciated that, in accordance with certain non-limiting embodiments of the present technology, the aligner 20 may be used for treating different teeth malocclusions, including but not limited to one or more of: closing interdental spaces ("space closure"), creating/widening interdental spaces, tooth rotation, tooth intrusion/extrusion, and tooth translation, to name a few. It should further be noted that in certain non-limiting embodiments of the present technology, applying the aligner 20 to upper teeth 16 may further include applying specific attachments thereto.

As may become apparent, the aligner 20 may be designed in such a way that its inner surface 12 is configured to impose respective forces on one or more of the upper teeth 16 to obtain a desired position of the upper teeth 16 at a given stage of the orthodontic treatment.

According to certain non-limiting embodiments of the present technology, the forces to be applied on the one or more teeth of the upper teeth 16 can be predetermined, based, for example, on 3D digital model of the upper arch form 10 (such as 3D mesh, as an example), in a current orthodontic treatment plan. To that end, as will become apparent from the description provided hereinbelow, the current orthodontic treatment plan may specify a tooth trajectory for each of the upper teeth 16 involved in the orthodontic treatment, such as for the given tooth 15, defining a path thereof from its initial position to its target position, typically associated with an alignment of the given tooth 15 within the upper teeth 16. Generally speaking, the tooth trajectory of the given tooth 15 can comprise a plurality of tooth segments, each of which is further associated with a respective force to be applied to the given tooth 15 to cause movement thereof along a given segment of the plurality of segments. Based on the planned displacement of the given tooth 15 along the given segment and the respective force to be applied therealong, a respective configuration of the aligner 20 can be produced for further implementation of the orthodontic treatment.

It is not limited how the current orthodontic treatment plan can be determined for the subject's teeth. For example, in some non-limiting embodiments of the present technology, the orthodontic treatment plan can be determined as described in a co-owned U.S. Pat. No. 10,993,782-B1, issued on May 4, 2021 and entitled "SYSTEMS AND METHODS FOR DETERMINING A TOOTH TRAJECTORY", content of which is incorporated herein by reference in its entirety. In another example, the respective orthodontic treatment can be determined by using one or more approaches described in a co-owned U.S. patent application Ser. No. 17/338,143, filed on Jun. 3, 2021 and entitled "SYSTEMS AND METHODS FOR DETERMINING AN ORTHODONTIC TREATMENT", content of which is incorporated herein by reference in its entirety.

Needles to say that, although in the depicted embodiments of FIGS. 2A and 2B, the aligner 20 is configured to be applied onto the upper teeth 16, in other non-limiting embodiments of the present technology, a respective configuration of the aligner 20 may be applied to lower teeth (not depicted) of the subject for treating misalignment of at least some thereof.

According to certain non-limiting embodiments of the present technology, the aligner 20 may be made of a polymer, such as a thermoplastic material. In other non-limiting embodiments of the present technology, the aligner 20 may be made of poly-vinyl chloride (PVC). In yet other non-limiting embodiments of the present technology, the aligner 20 may be made of polyethylene terephthalate glycol (PETG). Other suitable materials can also be used to form the aligner 20.

In some non-limiting embodiments of the present technology, the aligner 20 may be manufactured using additive manufacturing techniques, such as 3D printing techniques where the aligner 20 is formed by printing according to a pre-generated 3D digital models thereof.

In other non-limiting embodiments of the present technology, the aligner 20 may be produced by a thermoforming process where (1) an unfinished aligner is produced, using a preform, on a respective aligner mold (not depicted) associated with a respective stage of the orthodontic treatment, which is configured to shape the inner surface 12 of the aligner 20; and (2) the unfinished aligner is cut along a predetermined cut line to remove excess material therefrom, thereby producing the aligner 20, the predetermined cut line defining the at least one edge of the channel 18 of the aligner 20.

In specific non-limiting embodiments of the present technology, the aligner 20 may be manufactured in accordance with one or more methods described in a co-owned U.S. Pat. No. 11,191,618-B1, issued on Dec. 7, 2021 and entitled "SYSTEMS AND METHODS FOR FORMING A DENTAL APPLIANCE,", the content of which is incorporated herein by reference in its entirety.

However, during the implementation of the orthodontic treatment plan using the aligner 20, some of the upper teeth 16 may collide while displacing along their respective tooth trajectories. For example, with reference to FIG. 3, there is depicted a schematic diagram of the given tooth 15 caused to move towards the desired position thereof along a given segment 302 of its tooth trajectory according to the current orthodontic treatment plan, in accordance with certain non-limiting embodiments of the present technology.

Figure 3:
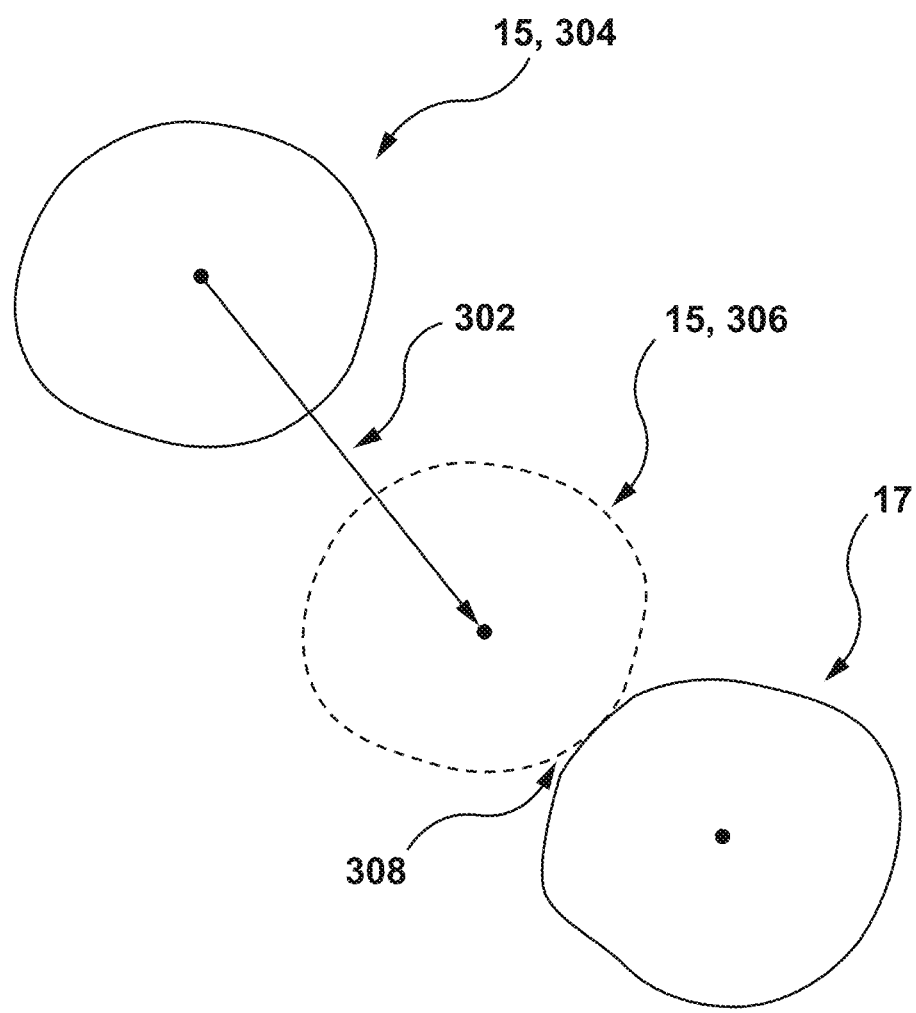
FIG. 3 depicts a schematic diagram of a given tooth of the subject's teeth present in FIG. 1 moving relative to a neighboring tooth and colliding therewith, in accordance with certain non-limiting embodiments of the present technology.

As it can be appreciated from FIG. 3, the given segment 302 is defined by a start position 304 and an end position 306, between which the given tooth 15 is caused to move under the respective force exerted by the aligner 20 towards the desired position, as described above. However, at the end position 306 of the given segment 302, the given tooth 15 can collide with a neighboring tooth, such as with the second adjacent tooth 17, forming a collision region 308 therewith.

The collision region 308 can be associated with excess pressure between the given tooth and the second adjacent tooth 17 causing discomfort to the subject, such as pain, in the course of the orthodontic treatment. Further, without preventing and/or resolving the so formed collision, the pressure in the collision region 308 can increase along with the progress of the current orthodontic treatment plan, causing other undesired side effects, such as cracks or chips on the enamel of at least one of the given tooth 15 and the second adjacent tooth 17.

Thus, it may be required, prior to the implementation of the current orthodontic treatment plan, to model tooth movements of the subject's teeth, such as using 3D meshes thereof, to identify the collisions therebetween. For example, one collision detection approach may include determining distances between respective vertices of 3D digital models of a given adjacent teeth (such as those depicted in FIG. 7, as an example) along the given segment of their tooth trajectories. Further, a minimum distance amongst the so determined distances can identified as being indicative of whether the given pair of adjacent teeth are positioned substantially close to each other for pre-emptively taking certain remedial actions for preventing a potential collision therebetween, which may include, without limitation, re-determining tooth trajectories thereof, stripping material from at least one of the given pair of adjacent teeth, or removal thereof. However, such an approach may be a resource-intensive task for a processor (such as a processor 550 depicted in FIG. 5) if implemented using 3D meshes of the given pair of adjacent teeth as it may be necessary to process a significant amount of graphic data representative of mesh vertices and/or mesh edges of the mesh elements.

Thus, certain non-limiting embodiments of the present technology are directed to methods and systems for determining collisions between the given pair of adjacent teeth, such as the given tooth 15 and the second adjacent tooth 17, using point cloud 3D digital models thereof, which comprise pluralities of points respectively representative of surfaces of the given tooth 15 and the second adjacent tooth 17. Further, the present methods include selective application of different approaches to determining the distances between points of each one of the given pair of adjacent teeth depending on a nature of relative movement between the given pair of adjacent teeth. More specifically, if it is determined that the given tooth 15 would move, along the given segment 302, translationally relative to the second adjacent tooth 17, the methods include determining the distances as distances between points representative of the given tooth 15 and a specifically determined plane associated with a side surface of the second adjacent tooth 17. By contrast, if it is determined that the given tooth 15, along the given segment 302, would move rotationally (or in other words, if the given segments 302 has a non-zero curvature), the present methods include generating, around the points representative of the second adjacent tooth 17, a distance field, and further determining the distances, from each point representative of the surface of the given tooth 15, to the surface of the second adjacent tooth 17 based on the distance field. By doing so, the methods and systems described herein may allow reducing the amount of graphic data to be processed for determining distances between the given pair of adjacent teeth without loss in accuracy. Thus, the methods and systems described herein can provide for a more efficient planning of the orthodontic treatment considering the safety thereof. By efficient planning is meant a faster processing of data to model the tooth movements to develop the orthodontic treatment for the subject.

How these different approaches are implemented, in accordance with certain non-limiting embodiments of the present technology, will be described in greater detail below with reference to FIGS. 6 to 10.

System

Figure 4:
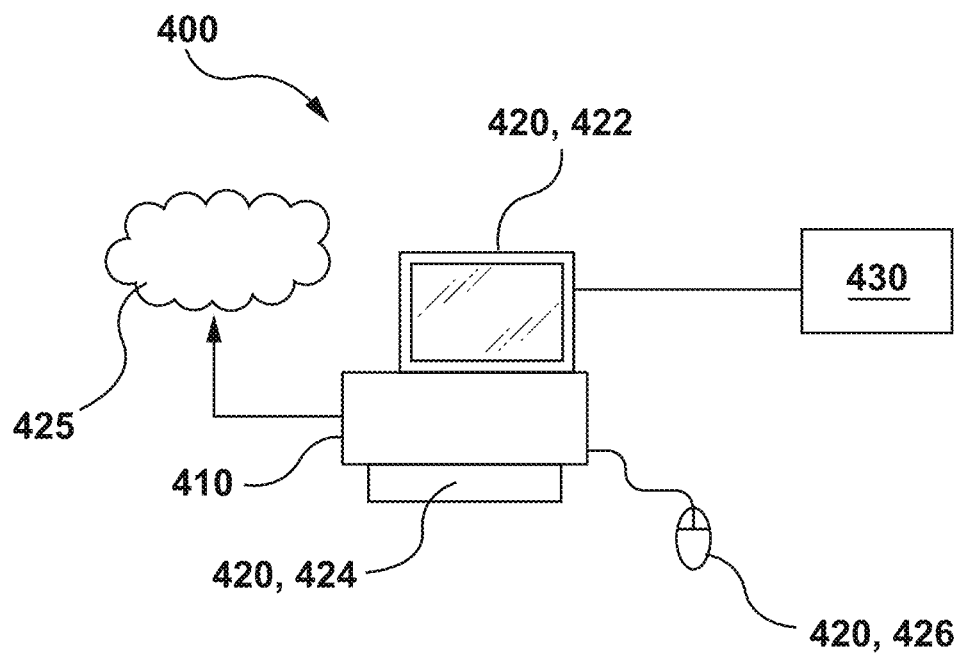
FIG. 4 depicts a schematic diagram of a system for determining an orthodontic treatment plan for the subject's teeth present in FIG. 1, in accordance with certain embodiments of the present technology.
Figure 5:
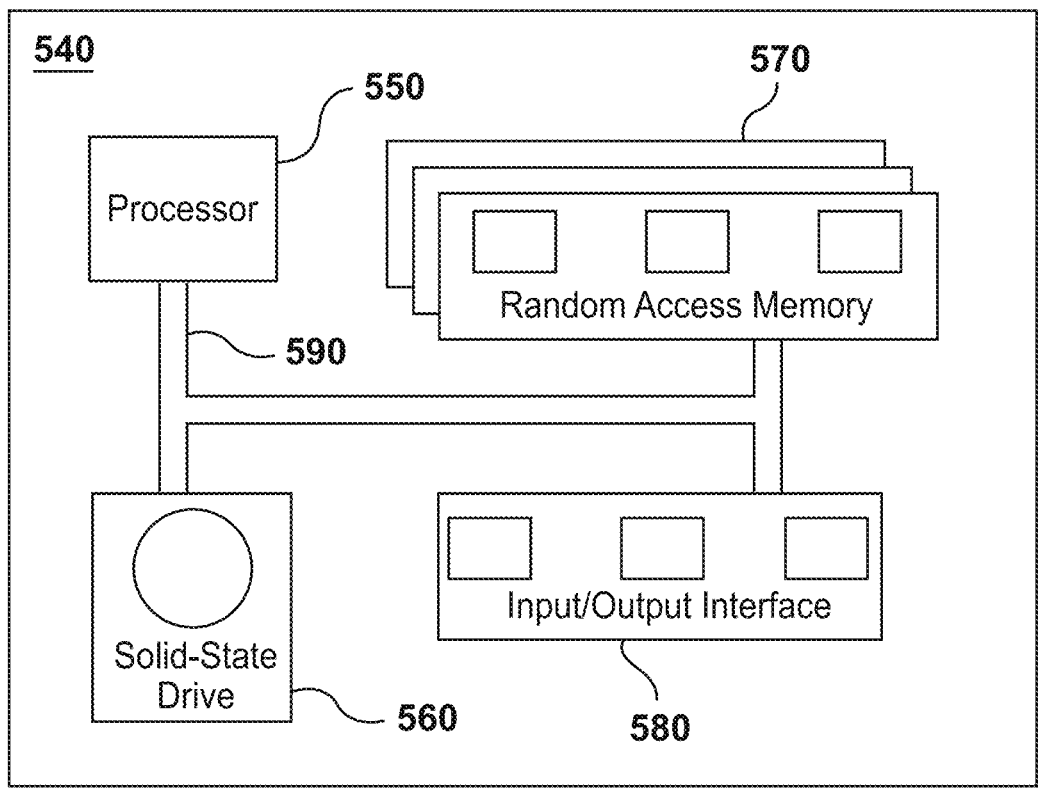
FIG. 5 depicts a schematic diagram of a computing environment of the system of FIG. 4, in accordance with certain embodiments of the present technology.

With reference to FIGS. 4 and 5, there is depicted a schematic diagram of a system 400 suitable for determining an orthodontic treatment for the subject, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to: (i) receive an indication of the current orthodontic treatment plan for the subject's teeth, such as for the upper teeth 16; (ii) determine, based on image data associated with the subject, such as the point cloud 3D representations, presence of collisions between the given pair of adjacent teeth, such as between the given tooth 15 and the second adjacent tooth 17 in the current orthodontic treatment plan; and (iii) updating the current orthodontic treatment plan resolving the collisions between the given tooth 15 and the second adjacent tooth 17. In additional non-limiting embodiments of the present technology, the computer system 410 may further be configured to model the movements of, for example, the given tooth 15 relative to the second adjacent tooth 17 determining distances between points representative thereof in real time for ensuring the aligner 20 produced based on the so planned orthodontic treatment would not cause any undesired effects to any one of the given tooth 15 and the second adjacent tooth 17 associated with the collisions therebetween, as described above.

To that end, in some non-limiting embodiments of the present technology, the computer system 410 may be configured to receive the image data pertaining to the subject or to a given stage of the current orthodontic treatment plan, such as that representative of the displacement of the given tooth 15 along the given segment 302, as described above. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of the given tooth 15 (e.g., a crown portion of the given tooth 15) extending outwardly of the gingival sulcus of the upper gingiva 36. In some embodiments, the image data is indicative of properties of internal portions of the anatomical structures, for example volumetric properties of bone surrounding an internal portion of the given tooth 15 (e.g., a root portion of the given tooth 15) extending inwardly of the gingival sulcus of the upper gingiva 36. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some non-limiting embodiments of the present technology, the image data includes datasets generally intended for the practice of periodontics.

In other non-limiting embodiments of the present technology, where the identifying the collisions between given pair of adjacent teeth is used for verifying the effect of the aligner 20 on the upper teeth 16, the image data may further include a 3D digital model of the aligner 20 prepared for manufacture thereof, for example, using 3D printing or thermoforming, as described above.

In some non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the upper teeth 16 and the periodontium (not depicted) of the subject. In certain non-limiting embodiments of the present technology, the image data may include, for example, one or more of: (1) images of external surfaces of respective crown portions of the upper teeth 16, (2) images of an external surface of the periodontium including those of the upper gingiva 36, the alveolar mandibular bone (not depicted), and images of superficial blood vessels and nerve pathways associated with the upper teeth 16; and (3) images of an oral region. By doing so, the imaging device 430 may be configured, for example, to capture image data of the upper arch form 10 of the subject. In another example, the imaging device may also be configured to capture and/or process image data of an upper arch form (not depicted) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions at least of the upper arch form 10 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 430 may comprise a desktop scanner enabling to digitize a mold (not depicted) representing the given configuration of the upper arch form 10 associated with the respective stage of the orthodontic treatment. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from DENTAL WINGS, INC. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 430 can comprise a 3D laser scanner enabling to obtain a respective point cloud 3D representation of the upper arch form 10—such as by scanning the mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, Minn. 55416. It should be expressly understood that the desktop scanner can be implemented in any other suitable equipment.

Further, it is contemplated that the computer system 410 may be configured for processing of the received image data. The resulting image data of the lower arch form 10 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (e.g. a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet™, Fibre Channel, Wi-Fi™ or Token Ring'. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Input Data

As alluded to above, according to certain non-limiting embodiments of the present technology, the processor 550 may be configured to: (1) receive image data indicative of the given pair of adjacent teeth within the upper arch form 10 corresponding to a given stage of the current orthodontic treatment plan; (2) determine, based on the image data, if the given pair of the adjacent teeth collide during the given stage of the current orthodontic treatment plan; and (3) update, based on the identified collisions, the current orthodontic treatment plan. Optionally, in some non-limiting embodiments of the present technology, the processor 550 may further be configured to cause the manufacture of the aligner 20 based on the so updated orthodontic treatment plan, as described above.

As noted hereinabove, in some-non-limiting embodiments of the present technology, using the imaging device 430, the processor 550 can be configured to obtain tooth 3D digital models of the given pair of adjacent teeth of the upper arch form 16, such as those of a first tooth 602 and a second tooth 604 depicted in FIGS. 6 and 7. For example, the first tooth 602 and the second tooth 604 can be equated to the given tooth 15 and the second adjacent tooth 17 described above. Thus, in those embodiments where the imaging device 430 is the CBCT scanner, as an example, the processor 550 may be configured to receive the tooth 3D digital models directly from the imaging device 430.

However, in other non-limiting embodiments of the present technology, where the imaging device 430 is the intra-oral scanner, for example, the processor 550 may be configured to generate the tooth 3D digital models of the first tooth 602 and the second tooth 604 based on a 3D digital model of a current configuration of the upper arch form 16 of the subject.

Figure 6:
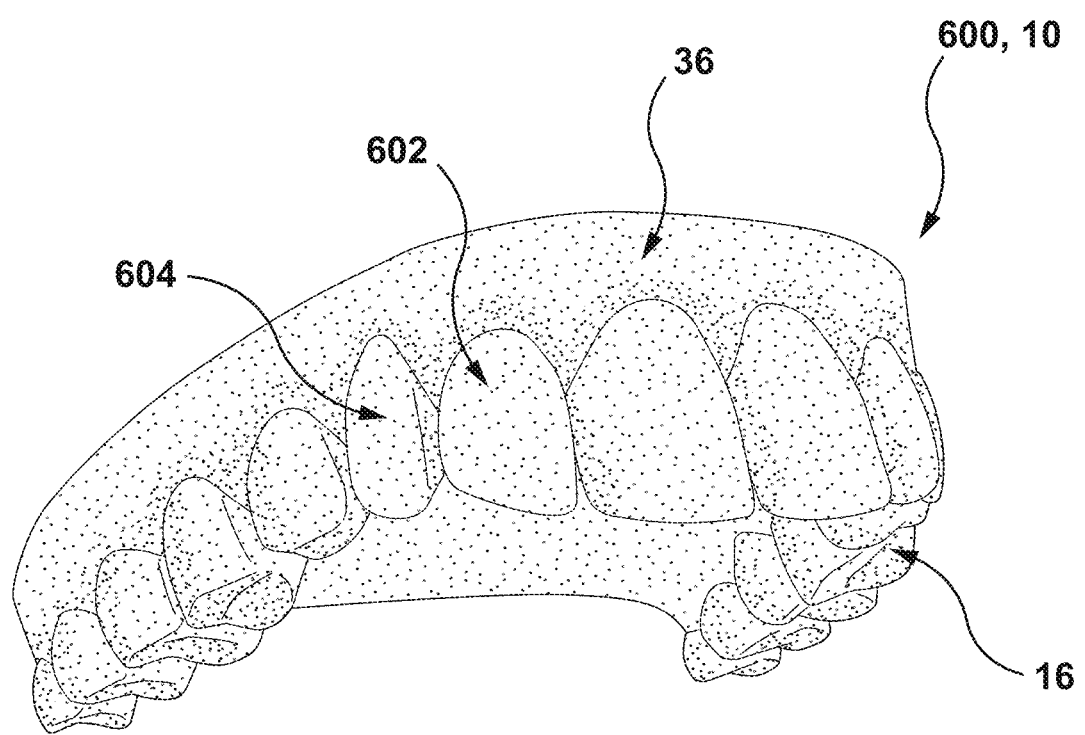
FIG. 6 depicts a 3D digital model including a point cloud representative of a surface of the upper arch form present in FIG. 1 used, by a processor of FIG. 5, to determine the orthodontic treatment plan for the subject, in accordance with certain non-limiting embodiments of the present technology.

With reference to FIG. 6, there is depicted a perspective view of an arch form 3D digital model 600 representative of a current configuration of the upper arch form 10, in accordance with certain non-limiting embodiments of the present technology.

As noted hereinabove, in some non-limiting embodiments of the present technology, the arch form 3D digital model 600 may be a point cloud 3D representation of the upper arch form 10 including a plurality of points representative of surfaces of the upper teeth 16 and the upper gingiva 36 of the subject.

In some non-limiting embodiments of the present technology where the imaging device 430 is the 3D laser scanner, the processor 550 may be configured to receive the arch form 3D digital model 600 as taken by the imaging device 430. In other non-limiting embodiments of the present technology, where the imaging device 430 is a conventional intraoral scanner providing 3D representations of objects including 3D meshes (such as triangular meshes and the like), the processor 550 may be configured to pre-process the arch form 3D digital model 600 to remove image data representative of the mesh edges therefrom leaving only image data representative of the mesh vertices.

It should be noted that it is not limited how points are distributed within the arch form 3D digital model 600; and in some non-limiting embodiments of the present technology, the points may be distributed uniformly within the arch form 3D digital model 600. However, in other non-limiting embodiments of the present technology, the points may have variable distribution within the arch form 3D digital model 600, such as have higher density in regions representative of the upper teeth 16 and have lower density in regions representative of upper gingiva 36.

Figure 7:
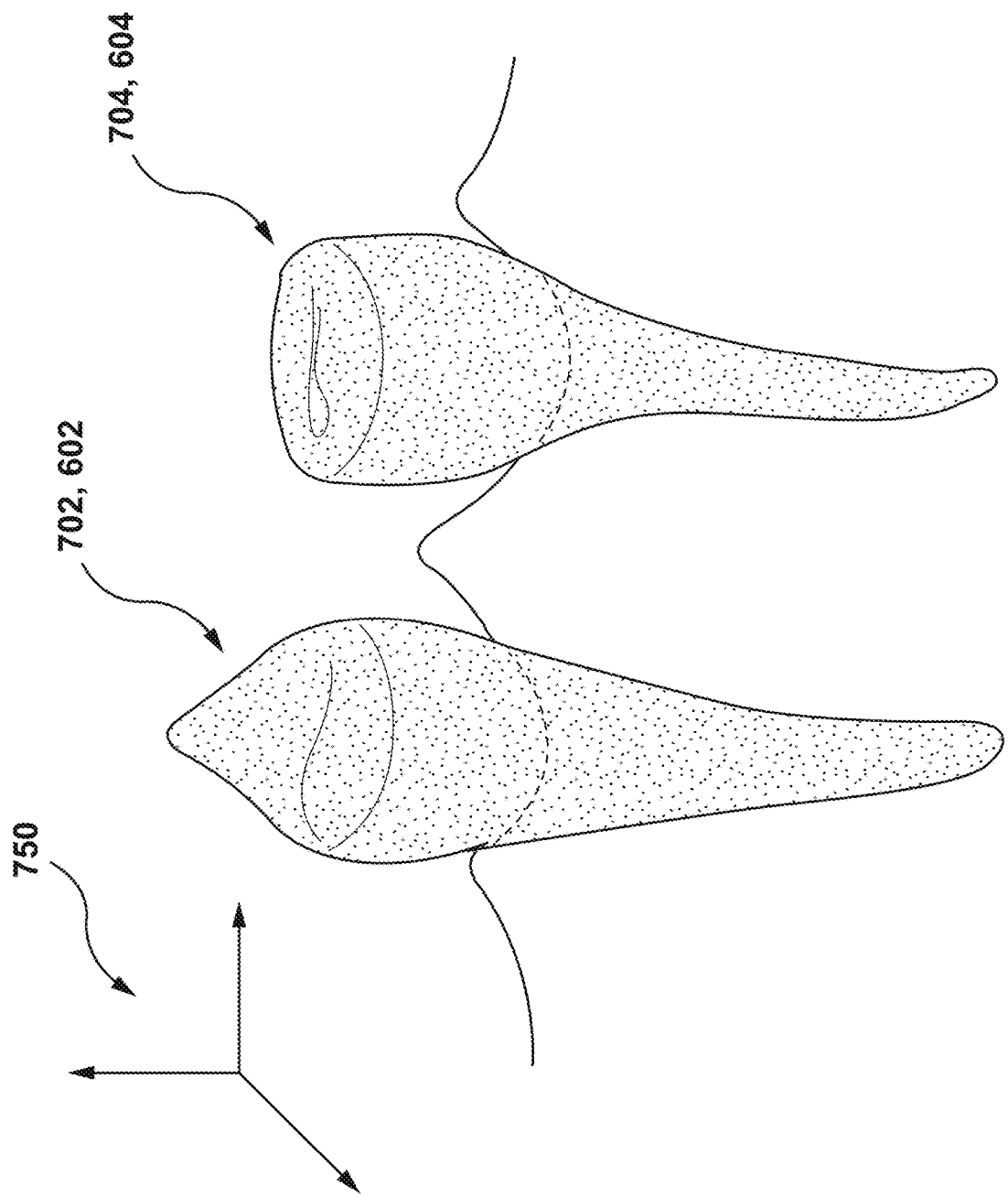
FIG. 7 depicts perspective 3D digital models of a given pair of adjacent teeth of the subject's teeth present in FIG. 1, generated, by the processor of FIG. 5, based on 3D digital model of the upper arch form of FIG. 6, in accordance with certain non-limiting embodiments of the present technology.

Further, according to certain non-limiting embodiments of the present technology, the processor 550 can be configured to generate, based on the 3D digital model 600, the tooth 3D digital models of the first tooth 602 and the second tooth 604—such as those schematically depicted, in accordance with certain non-limiting embodiments od the present technology, in FIG. 7, represented by a first plurality of vertices 702 and a second plurality of vertices 704, respectively.

To that end, the processor 550 can be configured to (i) isolate crown 3D digital models (not separately labelled) of crown portions of the first tooth 602 and the second tooth 604; generate (or otherwise, reconstruct), based on the so isolated crown portions, root 3D digital models (not separately labelled) of root portions of each one of the first tooth 602 and the second tooth 604; and (iii) merge respective crown 3D digital models and root 3D digital models, thereby generating tooth 3D digital models.

How the processor 550 can be configured to isolate the respective crown 3D digital model (not separately labelled) is not limited; and, in some non-limiting embodiments of the present technology, the processor 550 can be configured to apply, to the arch form 3D digital model 600, one or more automatic tooth segmentation approaches described in a co-owned U.S. Pat. No. 10,950,061-B1 issued on Mar. 16, 2021, entitled "SYSTEMS AND METHODS FOR PLANNING AN ORTHODONTIC TREATMENT", content of which is incorporated herein by reference in its entirety.

More specifically, to generate the respective crown 3D digital model of a given one of the first tooth 602 and the second tooth 604, the processor 550 may be configured to: (i) acquire the arch form 3D digital model 600 of the upper arch form 10 of the subject, the arch form 3D digital model 600 comprising a defined portion forming part of a surface of the given tooth 15, and at least one undefined portion not forming part of the surface of the given tooth 15; the arch form 3D digital model 600 comprising the plurality of mesh elements having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector; (ii) generate a set of confirmed constrained vertices, including the constrained vertices associated with the defined portion, for providing the respective crown 3D digital model of the crown portion a given one of the first tooth 602 and the second tooth 604 by: (iii) iteratively, for a given constrained vertex, identifying at least one associated unconstrained vertex which is adjacent to the given constrained vertex in the plurality of mesh elements; (iv) determining an angular difference between the normal constrained vertex vector of the given constrained vertex and the normal unconstrained vertex vector of the at least one associated unconstrained vertex; (v) in response to the angular difference being equal to or below a predetermined threshold value: identifying the at least one associated unconstrained vertex to be a constrained vertex associated with the defined portion for inclusion in the set of confirmed constrained vertices; (vi) in response to the angular difference being above the predetermined threshold value: identifying the at least one associated unconstrained vertex to be an unconstrained vertex associated with the undefined portion for exclusion from the set of Further, as noted above, optionally the processor 550 may be configured to generate the respective root 3D digital model of the root portion of the given one of the first tooth 604 and the second tooth 604 based on the respective crown 3D digital model obtained as described above. It is not limited how the processor 550 may be configured to generate the respective root 3D digital model of the root portions; however, in some non-limiting embodiments of the present technology, the processor 550 may be configured to generate the respective root 3D digital model of the given one of the first tooth 602 and the second tooth 604 based on reference data associated with the given tooth 15 applying one or more approaches described in a co-owned U.S. Pat. No. 11,026,767-B1, issued on Jun. 8, 2021 and entitled "SYSTEMS AND METHODS FOR PLANNING AN ORTHODONTIC TREATMENT", content of which is incorporated herein by reference in its entirety.

More specifically, in some non-limiting embodiments of the present technology, the reference data associated, for example, with the first tooth 602 may include, without limitation, at least one of a number of root branches of the root portion; approximate overall dimensions of the first tooth 602 including those of the crown portion and the root portion thereof. Also, in some non-limiting embodiments of the present technology, the reference data associated with the first tooth 602 may further include a base parametric 3D model of the root portion thereof and the processor 550 can be configured to generate the respective root 3D digital model of the root portion of the first tooth 602 based on the base parametric model.

Thus, the processor 550 can be configured to generate the tooth 3D digital models of each one of the first tooth 602 and the second tooth 604.

Further, as noted above, according to certain non-limiting embodiments of the present technology, the processor 550 can be configured to receive an indication of the current orthodontic treatment plan pre-determined for the subject. More specifically, the processor 550 can be configured to receive data indicative of tooth movements of at least one of the first tooth 602 and the second tooth 604 along their respective tooth trajectories from their current positions within the upper arch form 16, such as those represented by arch form 3D digital model 600, to their target, or desired positions, which may be associated with the alignment of the first tooth 602 and the second tooth 604 within the upper teeth 16, as an example.

In some non-limiting embodiments of the present technology, the respective tooth trajectories can be pre-generated based on minimizing time for each one of the first tooth 602 and the second tooth 604 to displace form their current positions to their target positions. For example, the time can be minimized within an acceptable time range predetermined such that a velocity of displacement of each one of the first tooth 602 and the second tooth 604 towards their target positions would not cause permanent damage to the subject's teeth and surroundings tissues, such as PDL, proximal nerve paths and blood vessels, as an example. More specifically, as noted above, the respective tooth trajectories of the first tooth 602 and the second tooth 604 can be determined using one of approaches described in one of U.S. Pat. No. 10,993,782-B1 and U.S. patent application Ser. No. 17/338,143 referenced above, as an example.

For example, the processor 550 can be configured to receive data indicative of tooth movements of the first tooth 602 at a given stage of the current orthodontic treatment plan. Such data, according to certain non-limiting embodiments of the present technology, may include data of the respective tooth trajectory of the first tooth 602 including a plurality of segments defining its path from the current position thereof within the upper arch form 16 towards a desired position of the first tooth 602, which can be expected from the implementation of the current orthodontic treatment plan.

Thus, according to certain non-limiting embodiments of the present technology, the data of the respective tooth trajectory may further include data of each one of the plurality of segments, such as, without limitation, an indication an end position for the first tooth 602 to arrive at along a given segment (such as that described with reference to FIG. 3 with respect to the given tooth 15), a force to be applied to the first tooth 602 during the implementation of the current orthodontic treatment plan causing the first tooth 602 to move towards the end position thereof along the given segment; and a time interval during which the force is to be applied to the first tooth 602.

In some non-limiting embodiments of the present technology, the tooth movements of the first tooth 602 can be movements of a given reference point (not separately depicted) thereof. In some non-limiting embodiments of the present technology, the given reference point cab selected to correspond to one of the first plurality of vertices 702 representative of a surface of the first tooth 602. In other non-limiting embodiments of the present technology, the given reference point can be selected to correspond to a center of resistance of the first tooth 602, which can be determined, by the processor 550, using one of approaches described, for example, in a co-owned U.S. Pat. No. 10,856,954-B1, issued Dec. 8, 2020 and entitled "SYSTEMS AND METHODS FOR DETERMINING TOOTH CENTER OF RESISTANCE", content of which is incorporated herein by reference in its entirety.

Further, according to certain non-limiting embodiments of the present technology, using the tooth 3D digital models of FIG. 7 and based on the respective tooth trajectories of the first tooth 602 and the second tooth 604, the processor 550 can be configured to determine, at the given stage of the current orthodontic treatment plan, relative movements, for example, of the first tooth 602 with respect to the second tooth 604 as the first tooth 602 moves along the given segment of its tooth trajectory. In other words, the processor 550 can be configured to determine the movements of the first tooth 602 along the given segment of its trajectory considering the second tooth 604 to be static.

To that end, in some non-limiting embodiments of the present technology, the processor 550 can be configured to define a coordinate system 750 associated with the first tooth 602. It is not limited how the processor 550 can be configured to define the coordinate system 750 for the first tooth 602; and in some non-limiting embodiments of the present technology, the processor 550 can be configured to define the coordinate system 750 to be a Cartesian coordinate system originating, for example, in the center of resistance of the first tooth 602. However, other types of the coordinate system 750, such as spherical or cylindrical, as well as other positions of the origin thereof within the first tooth 602 are also envisioned without departing from the scope of the present technology.

Thus, using the tooth 3D digital models of the first tooth 602 and the second tooth 604, as well as the data indicative of their tooth movements modelled for the current orthodontic treatment plan, the processor 550 can be configured to: (i) determine, based on the tooth 3D digital models, a distance between surfaces of the first tooth 602 and the second tooth 604 as the first tooth 602 moves along the given segment relative to the second tooth 604; (ii) determine, based on the distance, presence of a collision between the teeth during the implementation of the current orthodontic treatment plan, and (iii) update it in response to determining any occurrence of the collision, as will be described in detail below with reference to FIGS. 12 and 13.

According to certain non-limiting embodiments of the present technology, the processor 550 can be configured to apply different approaches to determining the distance between the teeth based on a nature of a current tooth movement of the first tooth 602 relative to the second tooth 604. In other words, the processor 550 can be configured to determine distance between the firs tooth 602 and the second tooth 604 differently depending on how the first tooth 602 moves along the given segment relative to the second tooth 604, such as rotationally or translationally, as will be described now with reference to FIGS. 8 to 11.

Collision Detection

Figure 8:
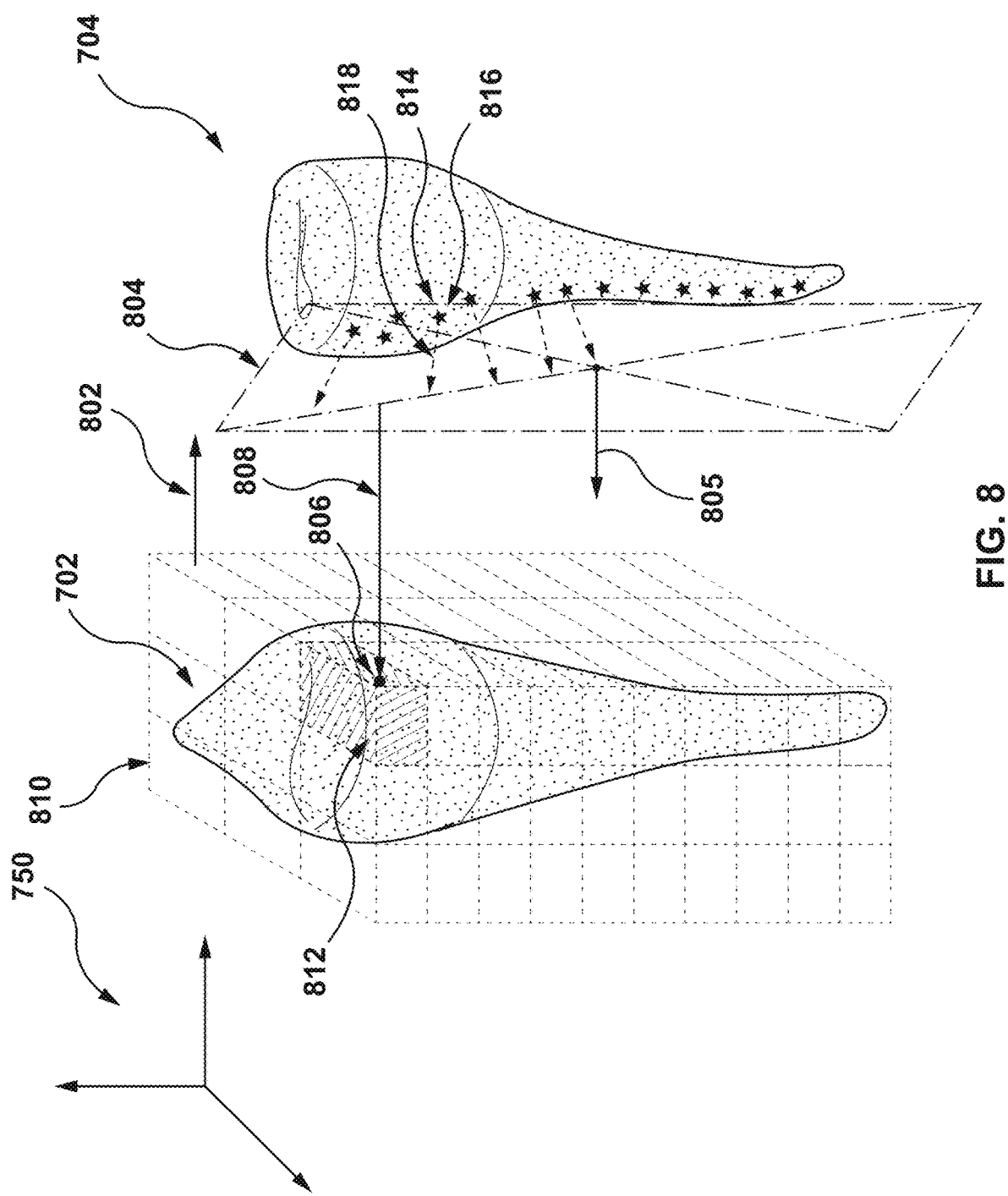
FIG. 8 depicts a schematic diagram of applying, by the processor of FIG. 5, a first approach to a distance between the given pair of adjacent teeth for determining an occurrence of the collision therebetween, in accordance with certain non-limiting embodiments of the present technology.

With reference to FIG. 8, there is depicted a schematic diagram of the processor 550 applying a first approach to determine the distance between the first tooth 602 and the second tooth 604, in accordance with certain non-limiting embodiments of the present technology.

For example, the processor 550 can be configured to determine, based on the input data described above, that the first tooth 602 moves translationally relative to the second tooth 604 along the given segment of its tooth trajectory, that is, along a given translational direction 802 within the coordinate system 750.

Thus, according to certain non-limiting embodiments of the present technology, the processor 550 can be configured to determine the distance between the surfaces of the first tooth 602 and the second tooth 604 based on respective linear distances from each one of the first plurality of vertices 702 to a reference plane 804 associated with a side surface of the second tooth 604 directed towards the first tooth 602 as it moves along the given segment.

How the processor 550 can be configured to determine the reference plane 804 is not limited and may comprise, for example, determining the reference plane 804 based on a set of reference vertices 814 of the second plurality of vertices 704 directed towards the first tooth 602. The processor 550 can be configured to select vertices from the second plurality of vertices 704 for inclusion in the set of reference vertices 814 based on directions of respective reference normal vectors thereat, such as a respective reference normal vector 818 at a given reference vertex 816, relative to the given translational direction 802. For example, the processor 550 can be configured to include the given reference vertex 816 in the set of reference vertices 814 if the respective reference normal vector 818 thereof is colinear with the given translational direction 802. In another example, the processor 550 can be configured to include the given reference vertex 816 in the set of reference vertices 814 if an angular difference between the respective reference normal vector 818 and the given translational direction 802 of then first tooth within the coordinate system 750 is not greater than a predetermined angular difference threshold, such as 1 or 2 degrees, as an example.

Further, in some non-limiting embodiments of the present technology, the processor 550 can be configured to determine the reference plane 804 as an average plane from the set of reference vertices 814, such as by averaging coordinates of each one of the set of reference vertices 814 in the coordinate system 750. In other non-limiting embodiments of the present technology, the processor 550 can be configured to determine the reference plane 804 as extending through certain outermost vertices of the set of reference vertices 814. In yet other non-limiting embodiments of the present technology, the processor 550 can be configured to determine the reference plane 804 as a plane extending through the most outermost vertex of the set of reference vertices 814 and parallel to a tooth axis (not depicted) associated with the second tooth 604. For example, the processor 550 can be configured to determine the tooth axis of the second tooth 604 as described in the U.S. Pat. No. 10,856,954-B1 referenced above. In yet other non-limiting embodiments of the present technology, the processor 550 can be configured to determine the reference plane 804 by determining a reference plane normal vector 805. For example, the reference plane normal vector 805 can be determined as an average vector of respective normal vectors associated with each one of the set of reference vertices 814.

Further, having determined the reference plane 804 associated with the side surface of the second tooth 604 directed towards the first tooth 602, in some non-limiting embodiments of the present technology, the processor 550 can be configured to determine the respective linear distances between each one of the first plurality of vertices 702 and the reference plane 804 along the reference plane normal vector 805—such as a respective linear distance 808 from a given vertex 806 of the first plurality of vertices 702.

However, in other non-limiting embodiments of the present technology, the processor 550 can be configured to determine the respective linear distances of only a set (not separately labelled) of the first plurality of vertices 702 directed towards the reference plane 804, which can be selected therefrom by the processor 550 as described above with respect to the set of reference plane 814.

Further, in some non-limiting embodiments of the present technology, the processor 550 can be configured to minimize a number of vertices of the first plurality of vertices 702 for determining the respective linear distances thereof to the reference plane 804.

To that end, according to certain non-limiting embodiments of the present technology, the processor 550 can be configured to generate a voxel grid 810 around the first plurality of vertices 702 including a plurality of voxels, each of which contains a respective portion of the first plurality of vertices 702—such as a given voxel 812. Further, the processor 550 can be configured to determine, in the given voxel 812, vertices that would be more representative of the collision between the surfaces of the first tooth 602 and the second tooth 604. Thus, having determined, in each voxel of the voxel grid 810, vertices of the first plurality of vertices 702 more representative of the collision between the surfaces of the first tooth 602 and the second tooth 604, the processor 550 can be configured to determine respective linear distances only from so determined vertices to the reference plane 804.

With reference to FIG. 9, there are depicted a lateral and horizontal projections the tooth 3D digital model of the first tooth 602, in accordance with certain non-limiting embodiments of the present technology.

For example, in some non-limiting embodiments of the present technology, the processor 550 can be configured to determine a respective single vertex 902 in the given voxel 812 for determining a respective linear distance therefrom to the reference plane 804. In some non-limiting embodiments of the present technology, the processor 550 can be configured to determine the respective single vertex 902 as an outermost vertex relative to a tooth axis (not depicted) of the first tooth 602. For example, to determine the respective single point 902, the processor 550 can be configured to apply a Bounding Volume Hierarchy algorithm.

However, in other non-limiting embodiments of the present technology, the processor 550 can be configured to determine a predetermined number, such as 3 or 4, outermost vertices in the given voxel 812 for determining respective linear distances thereof to the reference plane 804.

Further, in some non-limiting embodiments of the present technology, the processor 550 can be configured to determine the distance between the first tooth 602 and the second tooth 604 as being a minimum one of the respective linear distances. In some non-limiting embodiments of the present technology, in order to determine the minimum respective linear distance, the processor 550 can be configured to (1) organize the respective linear distances, for example, in a tree structure, and (2) apply a tree traversal search algorithm to the tree structure. In some non-limiting embodiments of the present technology, the tree traversal search algorithm may comprise a breadth-first search algorithm. Broadly speaking, the breadth-first search algorithm is a search algorithm configured to search a tree data structure for a node thereof meeting a predetermined condition—such as a condition of being indicative of the minimum respective linear distance in the tree structure representative of respective linear distances between the first plurality of vertices 702 and the reference plane 804 associated with the second tooth 604, as described above. The breadth-first search algorithm is configured to traverse all nodes at a given depth level of the tree data structure first prior to moving to a next depth level. However, it should be noted that in other non-limiting embodiments of the present technology, the implementation of the tree traversal search algorithm is not limited and may include, without limitation, a depth-first search algorithm, an iterative deepening depth-first search algorithm, a parallel breadth-first search algorithm, and others.

Thus, using the reference plane can allow not considering graphic data associated with the second plurality of vertices 704 for determining the distance between the surfaces of the first tooth 602 and the second tooth 604, which may allow reducing the computational burden on the processor 550. Further, by minimizing the number of vertices of the first plurality of vertices 702 for determining the respective linear distances therefrom to the reference plane 804 allows for additional reduction of computational resources consumption of the processor 550. This may thus allow the processor 550 to determine the distance between the surfaces of the first tooth 602 and the second tooth 604 in a more expeditious manner.

However, if the processor 550 has determined that, along the given segment of its tooth trajectory, the first tooth 602 does not move translationally relative to the second tooth, the processor 550 can be configured to determine the distance between the surfaces of the first tooth 602 and the second tooth 604 differently.

Figure 10:
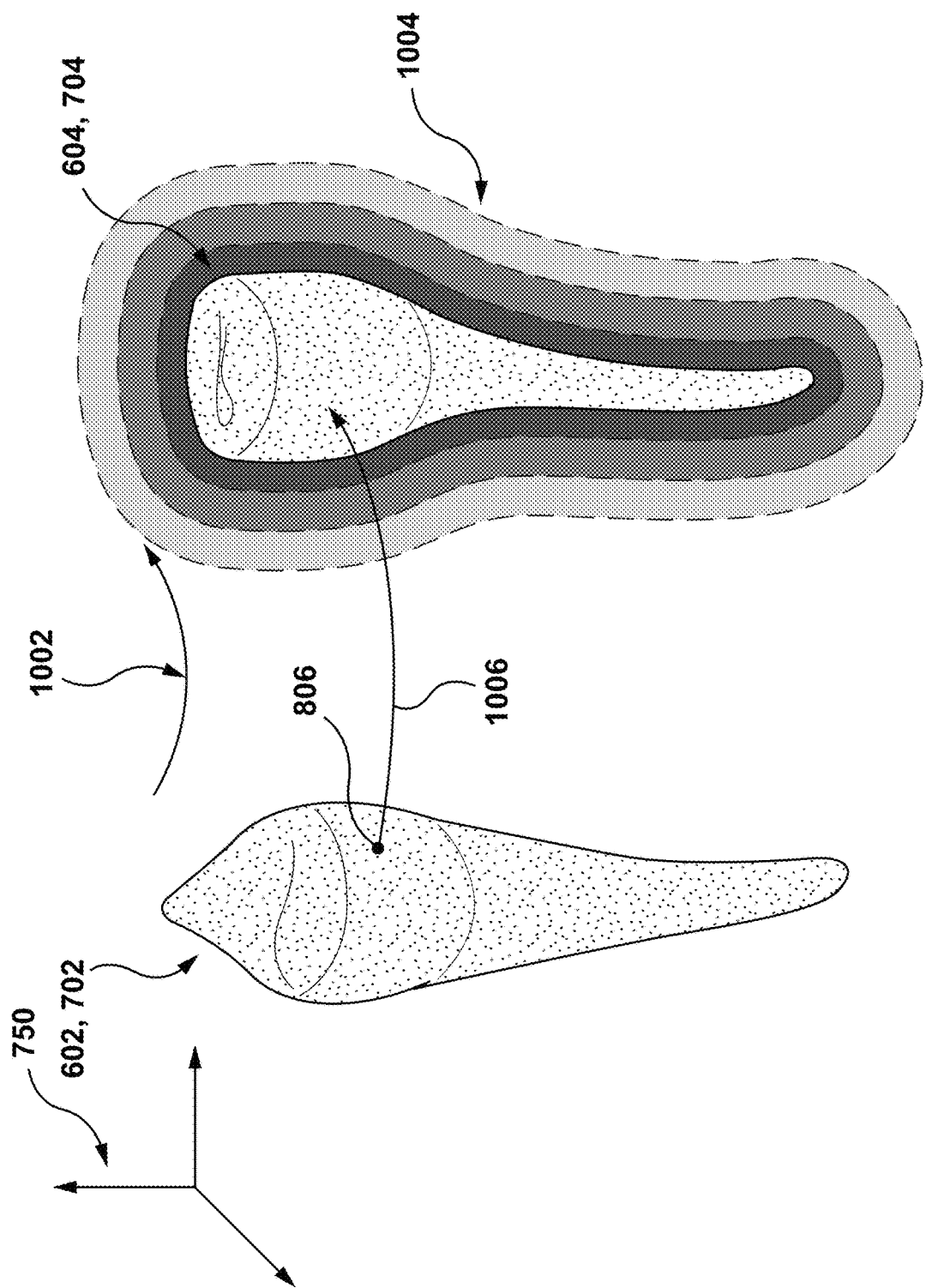
FIG. 10 depicts a schematic diagram of applying, by the processor of FIG. 5, a second approach to a distance between the given pair of adjacent teeth for determining the occurrence of the collision therebetween, in accordance with certain non-limiting embodiments of the present technology.

With reference to FIG. 10, there is depicted a schematic diagram of the processor 550 applying a second approach to determine the distance between the first tooth 602 and the second tooth 604, in accordance with certain non-limiting embodiments of the present technology.

For example, the processor 550 can be configured to determine that the first tooth 602 moves rotationally relative to the second tooth 604 in the coordinate system 750 associated with the first tooth 602—for example, along a given rotational direction 1002.

To that end, to determine the distance between the surfaces of the first tooth 602 and the second tooth 604, the processor 550 can be configured to determine respective arc distances from each one of the first plurality of vertices, such as the given vertex 806, to the surface of the second tooth 604 along the given rotational direction 1002. To do so, according to some non-limiting embodiments of the present technology, the processor 550 can be configured to define a distance field 1004 around the second plurality of points 704 representative of the surface of the second tooth 604.

In some non-limiting embodiments of the present technology, the distance field 1004 associated with the second tooth 604 can be a signed distance field. To that end, to determine the distance field 1004, the processor 550 can be configured to: (1) convert the second plurality of vertices 704 into a voxel space; (2) assign, to each voxel positioned inside the surface of the second tooth 604, a respective negative distance value from the surface of the second tooth 604; and (3) assign, to each voxel position outside the surface second tooth 604, a respective positive distance value from the surface of the second tooth 604.

Thus, the processor 550 may be configured to determine, based on the distance field 1004 so defined as described above, along the given rotational direction 1002, a respective arc distance 1006 from the given vertex 806 of the first plurality of vertices 702 to the surface of the second tooth 602.

As it may become apparent, in these embodiments, a level of accuracy of the determining the respective arc distance 1006 between the given vertex 806 and the surface of the second tooth 604 may depend on a level of granularity of the voxel space associated with the second plurality of vertices 704.

It should be noted similar to the case with the translational tooth movement of the first tooth 602 described above with reference to FIG. 8, when the first tooth 602 moves rotationally along the given segment of its tooth trajectory relative to the second tooth 604, the processor 550 can also be configured to minimize a number of vertices in the first plurality of vertices 702 for determining the respective arc distances therefrom to the surface of the second tooth 604.

Further, having determined the respective arc distances between the first plurality of vertices 702 and the surface of the second tooth 604, the processor 550 can be configured to determine the distance between the surfaces of the first tooth 602 and the second tooth 604 as being a minimum one of the respective arc distances, as described above with respect to the respective linear distances.

Further, according to certain non-limiting embodiments of the present technology, the processor 550 can be configured to determine if the so determined distance between the surfaces of the first tooth 602 and the second tooth 604 exceeds a predetermined distance threshold value, such as 0.1 to 0.5 mm, as an example. In response to determining that the distance exceeds the predetermined distance threshold value, the processor 550 can be configured to determine an occurrence of the collision between the first tooth 602 and the second tooth 604.

Thus, as determining the distance between the first tooth 602 and the second tooth 604 based on the distance field 1004, as described above, may be computationally costly, selectively applying the first approach to determining the distance in cases where the first tooth 602 moves, along the given segment of its tooth trajectory, translationally relative to the second tooth 604 allows reducing the computational burden on the processor 550, thereby reducing the time for determining the collision between the teeth.

Further, the processor 550 can be configured to examine each segment of the respective tooth trajectory of the first tooth 602 for occurrences of the collision therein with the second tooth 604 by further modelling the tooth movements of the first tooth 602 relative to the second tooth 604 in the course of the current orthodontic treatment plan, as described above. By doing so, the processor 550 can be configured to determine certain parameters of the so formed collision between the first tooth 602 and the second tooth 604 to further take certain preventive actions for resolving the collision, as will be described below.

Figure 11:
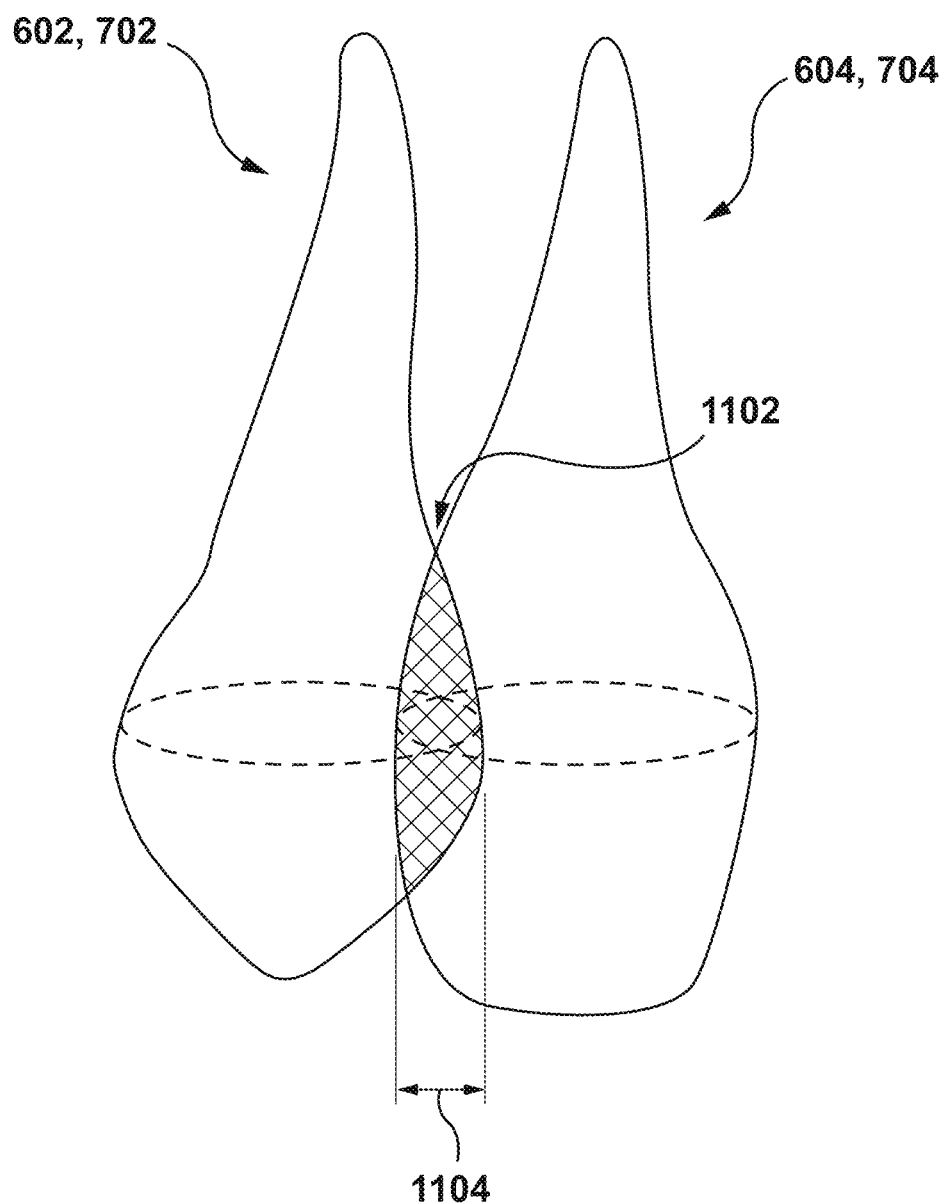
FIG. 11 depicts a schematic diagram of determining, by the processor of FIG. 5, a degree of penetration between the given pair of adjacent teeth, in accordance with certain non-limiting embodiments of the present technology.

For example, with reference to FIG. 11, in some non-limiting embodiments of the present technology, the processor 550 can be configured to determine, based on the first plurality of vertices 702 and the second plurality of vertices 704, presence of an overlap region 1102 between the first tooth 602 and the second tooth 604 as the first tooth 602 moves along the given segment of its tooth trajectory according to the current orthodontic treatment plan.

Further, in some non-limiting embodiments of the present technology, based on the tooth 3D digital models, the processor 550 can be configured to determine a respective degree of penetration 1104 (for example, in mm) between the first tooth 602 and the second tooth 604 caused by the identified collision as the first tooth 602 moves along the given segment of its tooth trajectory. Thus, in some non-limiting embodiments of the present technology, the processor 550 can further be configured to determine a maximum degree of penetration between the first tooth 602 and the second tooth 604 as the first tooth 602 moves along each segment of its tooth trajectory according to the current orthodontic treatment plan.

Further, the processor 550 can be configured to determine a collision time interval, during which the first tooth 602 and the second tooth 604 would be colliding as the first tooth 602 moves along the given segment of its tooth trajectory according to the current orthodontic treatment plan.

Further, in some non-limiting embodiments of the present technology, the processor 550 can be configured to map indications of at least some of the so determined parameters onto an indication of the current orthodontic treatment plan for visualization of the so identified collision between the first tooth 602 and the second tooth 604, as will described now.

Collision Visualization

Figure 12:
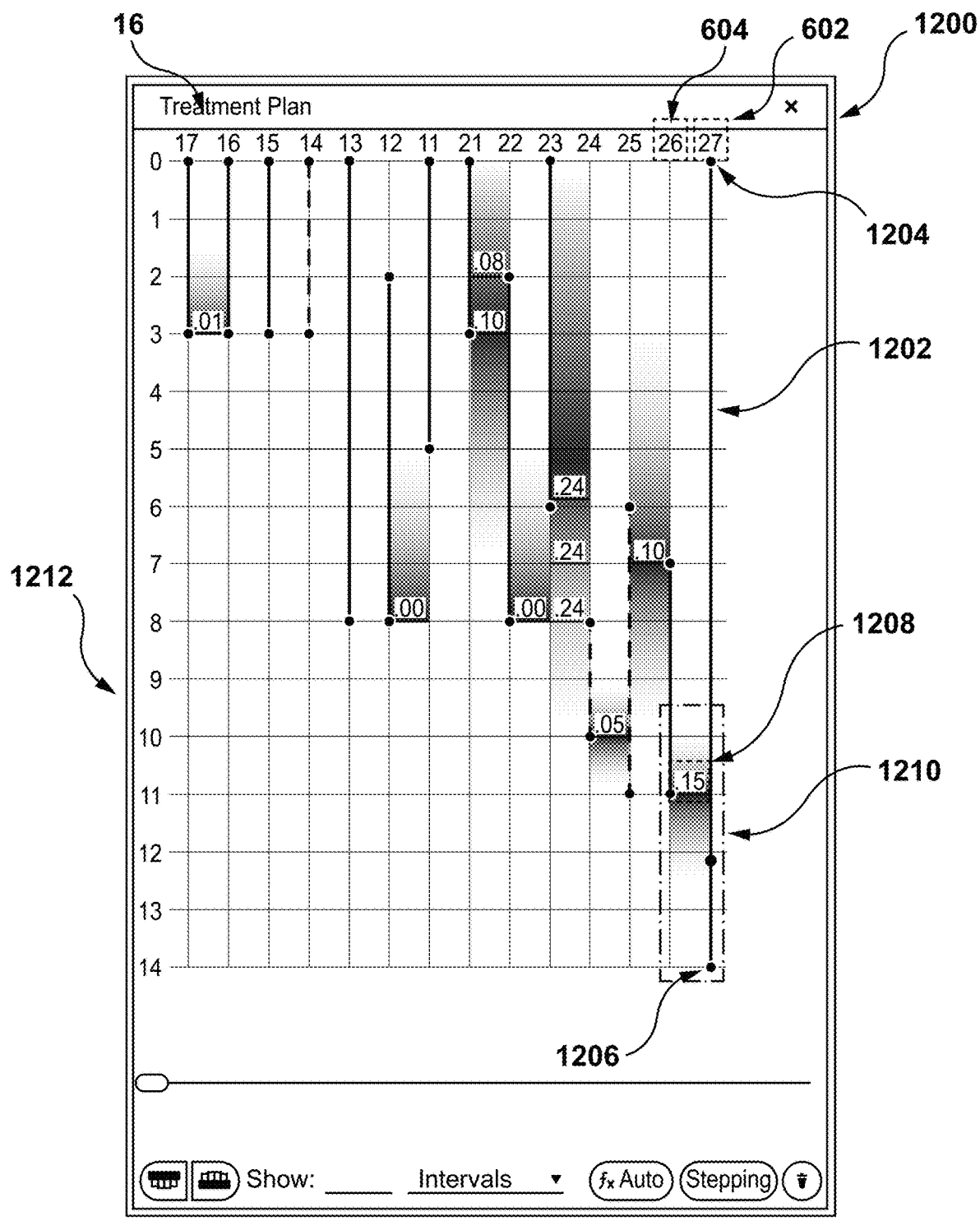
FIG. 12 depicts a schematic implementation diagram of a current orthodontic treatment plan for the subject including indications of the collision between the given pair of adjacent teeth, in accordance with certain non-limiting embodiments of the present technology.

With reference to FIG. 12, there is schematically depicted an implementation diagram 1200 of the current orthodontic treatment plan for the upper teeth 16 of the subject, in accordance with certain non-limiting embodiments of the present technology.

For example, the processor 550 can be configured to generate the implementation diagram 1200 based on using various configurations of the aligner 20 for causing those of the upper teeth 16 involved in the orthodontic treatment to move along their tooth trajectories, as described, for example, in the U.S. Pat. No. 10,993,782-B1 referenced above.

According to certain non-limiting embodiments of the present technology, an X axis of the implementation diagram 1200 is representative of ordinal numbers of the upper teeth 16, and a Y axis of the implementation diagram 1200 is representative of stages of the current orthodontic treatment plan, such as from 0 to 14, as depicted in FIG. 12, as an example. More specifically, in accordance with certain non-limiting embodiments of the present technology, each stage of the current orthodontic treatment plan can correspond to a respective treatment interval, during which a respective configuration of the aligner 20 can be applied to cause those of the upper teeth 16 involved in the orthodontic treatment to move along their tooth trajectory.

For example, the implementation diagram 1200 may have a trajectory visual representation 1202 of the respective tooth trajectory of the first tooth 602, including: (i) an initial position indication 1204 of the first tooth 602 corresponding to an initial stage of the current orthodontic treatment plan (which is denoted by '0' along the Y axis in the example of FIG. 12); and (ii) a target position indication 1206 of the first tooth 602 corresponding to a final stage of the current orthodontic treatment plan (which is denoted by '14' along the Y axis in the example of FIG. 12).

Further, while moving along the given segment of its tooth trajectory, such as that corresponding to a respective treatment interval 1212, the first tooth 602 can collide with the second tooth 604. In this regard, as described above, in some non-limiting embodiments of the present technology, the processor 550 can be configured to determine a value 1208 of the total maximum degree of penetration between the first tooth 602 and the second tooth 604 during the implementation of the current orthodontic treatment plan, and map the value 1208 onto the implementation diagram 1200, which, in the present example of FIG. 12, is 0.15 mm. For example, the processor 550 can be configured to map the value 1208 onto a portion of the trajectory visual representation 1202 of the respective tooth trajectory of the first tooth 602 corresponding to a segment thereof where the maximum degree of penetration between the first tooth 602 and the second tooth 604 is attained.

However, in other non-limiting embodiments of the present technology, instead of mapping the value 1208 of the maximum degree of penetration, the processor 550 can be configured to map, onto the trajectory visual representation 1202, values of the respective degrees of penetration associated with each segment of the respective tooth trajectory of the first tooth 602 where the collision between the first tooth 602 and the second tooth 604 has been identified, such as the respective degree of penetration 1104 associated with the given segment, as described above.

Further, as noted above, according to certain non-limiting embodiments of the present technology, the processor 550 can be configured to map, onto the implementation diagram 1200 of the current orthodontic treatment plan, a time interval visual representation 1210 of the collision time interval, which, in the example of FIG. 12, begins in the respective treatment interval 1212 and ends at the final stage of the current orthodontic treatment plan.

Further, according to certain non-limiting embodiments of the present technology, after detecting the collision between the first tooth 602 and the second tooth 604, as described above, the processor 550 can be configured to take certain preventive actions to resolve the collision, thereby updating the current orthodontic treatment plan, as will now be described.

Collision Resolution and Treatment Plan Update

In one example, the processor 550 can be configured to generate a request for re-determining the respective tooth trajectory of at least one of the first tooth 602 and the second tooth 604 such that new tooth trajectories thereof would not allow the teeth to collide during the implementation of the updated orthodontic treatment plan. The re-determining the respective tooth trajectory, for example, of the first tooth 602, may include, without limitation, modifying the force to be applied to the first tooth at the given stage of the current orthodontic treatment plan, including one or both of a magnitude and direction thereof, thereby modifying the tooth movements of the first tooth 602 relative to the second tooth 604 as the first tooth 602 moves along the given segment, as described above, such that the occurrence of the collision therein with the second tooth 604 would be avoided. In another example, the re-determining the respective tooth trajectory may include modifying a number of segments of the respective tooth trajectory of the first tooth 602 allowing, for example, bypassing the collision thereof with the second tooth 604.

However, in cases where the redetermining the tooth trajectories is impossible and/or undesirable, according to certain non-limiting embodiments of the present technology, the processor 550 can be configured to add, in the current orthodontic treatment plan, a stripping request for stripping tooth material of at least one of the first tooth 602 and the second tooth 604 sufficient for avoiding the collision without re-determining the tooth trajectories thereof. More specifically, the stripping request may include prescription of physical removal, such as by milling, of the tooth material from the at least one of the first tooth 602 and the second tooth 604, at a certain stage of the current orthodontic treatment plan, for example, prior to a first occurrence of the collision between the first tooth 602 and the second tooth 604 in the current orthodontic treatment plan. For example, the processor 550 can be configured to add and validate the stripping request in accordance with one of the approaches described in a co-owned U.S. patent application Ser. No. 17/667,304 filed concurrently with the present application and entitled "SYSTEMS AND METHODS FOR DETERMINING AN ORTHODONTIC TREATMENT PLAN", content of which is incorporated herein by reference in its entirety.

According to certain non-limiting embodiments of the present technology, the processor 550 can be configured to determine an amount of the tooth material to be removed from the at least one of the first tooth 602 and the second tooth 604 for resolving the collision therebetween based on the value 1208 of the maximum degree of penetration therebetween during the collision time interval, as explained above with reference to FIGS. 11 and 12. For example, returning back to the examples of FIGS. 11 and 12, the processor 550 can be configured to generate the stripping request for stripping, from side surfaces of the at least one of the first tooth 602 and the second tooth 604 defining the overlap region 1102, an amount of tooth material equal to at least 0.15 mm along occlusal surfaces of the teeth.

In some non-limiting embodiments of the present technology, depending, for example, on a configuration of the overlap region 1102, the stripping request can include stripping the so determined amount of the tooth material only from the first tooth 602 or only from the second tooth 604. In other non-limiting embodiments of the present technology, this amount of the tooth material can be stripped, in a certain proportion, such as 50/50, from each one of the first tooth 602 and the second tooth 604. Thus, by adding the stripping request to the current orthodontic treatment plan, the processor 550 can be configured to generate the updated orthodontic treatment plan.

Figure 13:
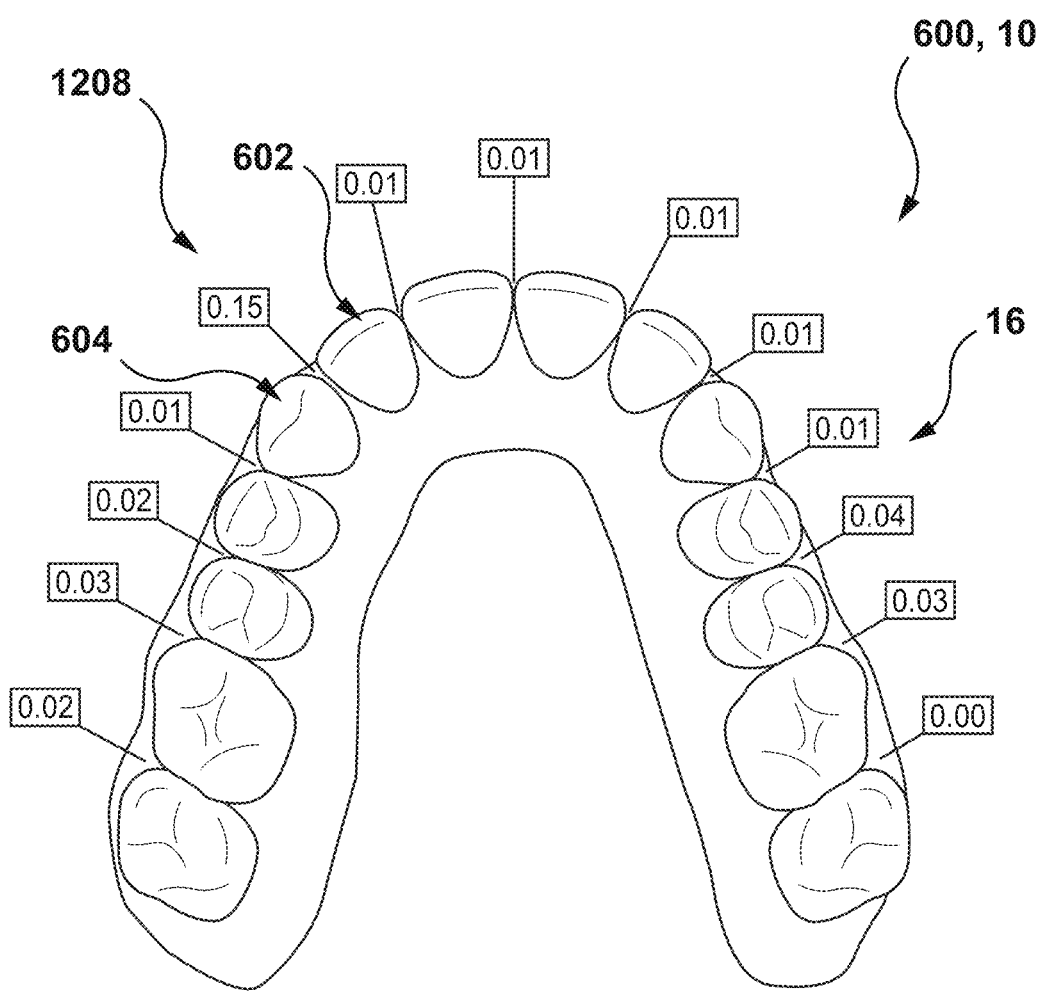
FIG. 13 depicts the 3D digital model of the upper arch form present in FIG. 1 with indications of tooth material to be preventively stripped for resolving the collision between the given pair of adjacent teeth indicated in FIG. 12, in accordance with certain non-limiting embodiments of the present technology.

Further, in additional non-limiting embodiments of the present technology, the processor 550 can be configured to cause display of the stripping request over the arch form 3D digital model 600, as schematically depicted in FIG. 13, in accordance with certain non-limiting embodiments of the present technology. Further, based on the so visualized stripping request, an orthodontic practitioner, for example, can prescribe that the subject have the indicated amount of the tooth material corresponding to the value 1208 of the maximum degree of penetration removed from the at least one of the first tooth 602 and the second tooth 604.

In yet other non-limiting embodiments of the present technology, where the stripping request cannot be executed safely, as an example, the processor 550 can be configured to add, in the current orthodontic treatment plan, a removal request for prescribing removal of at least one of the first tooth 602 and the second tooth 604 at a certain stage of the current orthodontic treatment plan prior to the first occurrence of the collision between the teeth, thereby generating the updated orthodontic treatment plan.

Further, based on the so updated orthodontic treatment plan, the processor 550 can be configured to determine a respective configuration of the aligner 20 to be applied to the upper teeth 16 to cause the first tooth 602 to move towards the target position thereof without causing the collision thereof with the second tooth 604. For example, the processor 550 can be configured to determine configuration of the aligner 20 and further cause manufacture thereof, for example as described in the U.S. Pat. No. 11,191,618-B1 referenced above.

Thus, the processor 550 can be configured to determine the collision between the first tooth 602 and the second tooth 604 in the current orthodontic treatment plan and further cause execution of certain preventive actions for resolving the collision and thus generate the updated orthodontic treatment plan.

Method

Figure 14:
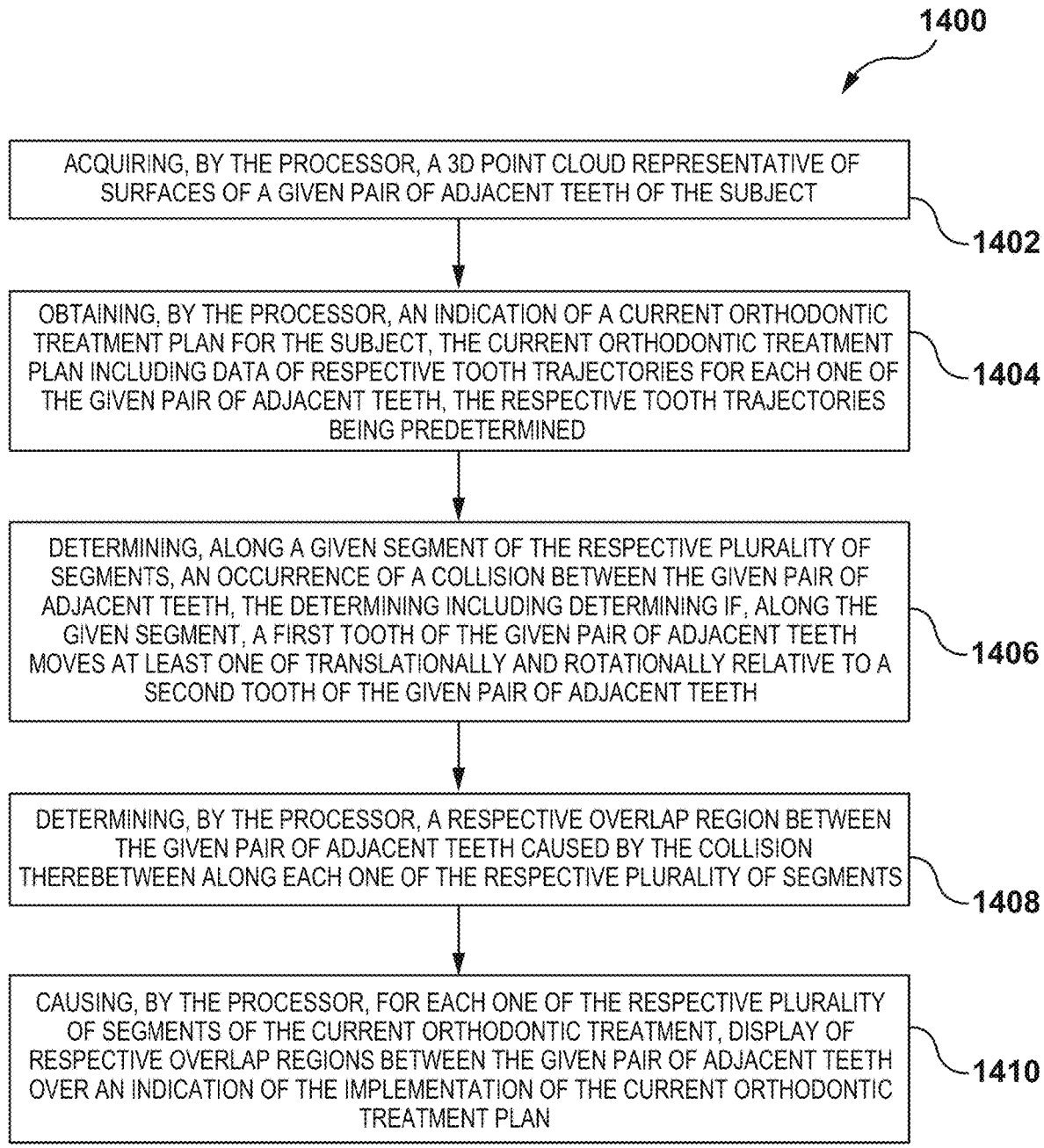
FIG. 14 depicts a flowchart of a method of determining the orthodontic treatment plan for the subject's teeth present in FIG. 1, according to certain embodiments of the present technology.

Given the architecture and the examples provided hereinabove, it is possible to execute a method for determining an orthodontic treatment plan for the subject. With reference now to FIG. 14, there is depicted a flowchart of a method 1400, according to certain non-limiting embodiments of the present technology. The method 1400 may be executed by the processor 550 of the system 400.

Step 1402: Acquiring, by the Processor, a 3D Point Cloud Representative of Surfaces of a Given Pair of Adjacent Teeth of the Subject The method 1400 commences at step 1402 with the processor 550 being configured to acquire a 3D point cloud representative of the given pair of adjacent teeth of the subject, such as the first tooth 602 and the second tooth 604. As mentioned above, in accordance with certain non-limiting embodiments of the present technology, the processor 550 can be configured to generate such a 3D point cloud based on the arch form 3D digital model 600 received, for example, from the imaging device 430, as described above.

For example, in some non-limiting embodiments of the present technology where the imaging device 430 is the 3D laser scanner, the processor 550 may be configured to receive the arch form 3D digital model 600 as taken by the imaging device 430. In other non-limiting embodiments of the present technology, where the imaging device 430 is a conventional intraoral scanner providing 3D representations of objects including 3D meshes (such as triangular meshes and the like), the processor 550 may be configured to pre-process the arch form 3D digital model 600 to remove image data representative of the mesh edges therefrom leaving only image data representative of the mesh vertices.

Further, as described above with reference to FIG. 6, the processor 550 can be configured to identify, within the arch form 3D digital model 600, the first plurality of vertices 702 and the second plurality of vertices 704 representative of the first tooth 602 and the second tooth 604, respectively.

The method 1400 thus advances to step 1404.

Step 1404: Obtaining, by the Processor, an Indication of a Current Orthodontic Treatment Plan for the Subject, the Current Orthodontic Treatment Plan Including Data of Respective Tooth Trajectories for Each One of the Given Pair of Adjacent Teeth, the Respective Tooth Trajectories being Predetermined Further, at step 1404, the processor 550 can be configured to receive the indication of the current orthodontic treatment plan including data of the respective tooth trajectory of each one of the first tooth 602 and the second tooth 604 defining paths thereof from their current positions to their target, or desired, positions.

In some non-limiting embodiments of the present technology, the respective tooth trajectories can be pre-generated based on minimizing time for each one of the first tooth 602 and the second tooth 604 to displace form their current positions to their target positions. For example, the time can be minimized within an acceptable time range predetermined such that a velocity of displacement of each one of the first tooth 602 and the second tooth 604 towards their target positions would not cause permanent damage to the subject's teeth and surroundings tissues, such as PDL, proximal nerve paths and blood vessels, as an example. More specifically, as noted above, the respective tooth trajectories of the first tooth 602 and the second tooth 604 can be determined using one of approaches described in one of U.S. Pat. No. 10,993,782-B1 and U.S. patent application Ser. No. 17/338,143 referenced above, as an example.

Thus, the respective tooth trajectory, for example, of the first tooth 602, can comprise the plurality of segments, along which the first tooth is to be caused to move from its current position to its target position in the course of implementation of the current orthodontic treatment plan. Further, as mentioned further above, the data of the respective tooth trajectory received by the processor 550 can further include data of each one of the plurality of segments, such as, without limitation, an indication an end position for the first tooth 602 to arrive at along the given segment (such as that described with reference to FIG. 3 with respect to the given tooth 15), a force to be applied to the first tooth 602 during the implementation of the current orthodontic treatment plan causing the first tooth 602 to move towards the end position thereof along the given segment; and a time interval during which the force is to be applied to the first tooth 602.

The method 1400 hence advances to step 1406.

Step 1406: Determining, Along a Given Segment of the Respective Plurality of Segments of at Least One of the Given Pair of Adjacent Teeth, an Occurrence of a Collision Between the Given Pair of Adjacent Teeth, the Determining Including Determining if, Along the Given Segment, a First Tooth of the Given Pair of Adjacent Teeth Moves at Least One of Translationally and Rotationally Relative to a Second Tooth of the Given Pair of Adjacent Teeth Further, at step 1406, according to certain non-limiting embodiments of the present technology, the processor 550 can be configured to determine if while moving along the given segment of its respective tooth trajectory, the first tooth 602 collides with the second tooth 604. According to certain non-limiting embodiments of the present technology, to determine an occurrence of the collision between the first tooth 602 and the second tooth 604 as they are moving along their respective tooth trajectories, the processor 550 can be configured to determine the distance between surfaces thereof represented by the first plurality of vertices 702 and the second plurality of vertices 704, respectively.

According to certain non-limiting embodiments of the present technology, as mentioned above with reference to FIGS. 8 to 10, the processor 550 can be configured to determine the distance between the surfaces of the first tooth 602 and the second tooth 604 applying different approaches based on the nature of their movement relative to each other.

More specifically, in response to determining, based on the input data received at steps 1402 and 1404, that along the given segment of its respective tooth trajectory, the first tooth 602 moves translationally relative to the second tooth 604, the processor 550 can be configured to determine the distance between the surfaces thereof by determining the respective linear distances between the first plurality of vertices 702 and the reference plane 804 associated with the side surface of the second tooth 604, as described in detail above with reference to FIG. 8.

Also, in additional non-limiting embodiments of the present technology, the processor 550 can be configured to minimize the number of vertices from the first plurality of vertices 702, using the voxel grid 810 defined therearound, for determining the respective linear distances therefrom to the reference plane 804, as described in detail further above with reference to FIG. 9.

Further, in some non-limiting embodiments of the present technology, the processor 550n can be configured to determine the distance between the surfaces of the first tooth 602 and the second tooth 604 as being the minimum respective linear distance, for example, by applying the tree traversal search algorithm.

However, if the processor 550 has determined that, along the given segment of its tooth trajectory, the first tooth 602 does not move translationally relative to the second tooth, the processor 550 can be configured to determine the distance between the surfaces of the first tooth 602 and the second tooth 604 differently.

More specifically, as described in detail above with reference to FIG. 10, in response to determining that the first tooth 602 moves rotationally relative to the second tooth along the given segment of its respective toot trajectory, such as along the given rotational direction 1002, the processor 550 can be configured to determine the distance between the surfaces thereof based on the respective arc distance along the given rotational direction 1002. To that end, according to certain non-limiting embodiments of the present technology, the processor 550 can be configured to generate the distance field 1004 around the second plurality of vertices 704 representative of the surface of the second tooth 604.

As it can be appreciated, as it is the case with determining the respective linear distances, in certain non-limiting embodiments of the present technology, the processor 550 can be configured to minimize the number of vertices from the first plurality of vertices 702 for determining the respective arc distances as described above with reference to FIG. 9, as well.

Further, the processor 550 can be configured to determine the distance between the surfaces of the first tooth 602 and the second tooth 604 as being the minimum respective arc distance, in a similar fashion to determining the minimum respective linear distance.

Further, according to certain non-limiting embodiments of the present technology, the processor 550 can be configured to determine if the so determined distance between the surfaces of the first tooth 602 and the second tooth 604 exceeds the predetermined distance threshold value, such as 0.1 to 0.5 mm, as an example. In response to determining that the distance exceeds the predetermined distance threshold value, the processor 550 can be configured to determine an occurrence of the collision between the first tooth 602 and the second tooth 604.

Thus, as determining the distance between the first tooth 602 and the second tooth 604 based on the distance field 1004, as described above, may be computationally costly, selectively applying the first approach to determining the distance in cases where the first tooth 602 moves, along the given segment of its tooth trajectory, translationally relative to the second tooth 604 allows reducing the computational burden on the processor 550, thereby reducing the time for determining the collision between the teeth.

The method 1400 thus proceeds to step 1408.

Step 1408: Determining, by the Processor, a Respective Overlap Region Between the Given Pair of Adjacent Teeth Caused by the Collision Therebetween Along the Given Segment Further, at step 1408, by applying step 1406 to other segments of the respective tooth trajectory of the first tooth 602, the processor 550 can be configured to determine other occurrences of the collision between the first tooth 602 and second tooth 604 in the course of the current orthodontic treatment plan. By doing so, the processor 550 can be configured to determine certain parameters of the so formed collision between the first tooth 602 and the second tooth 604 to further take certain preventive actions for resolving the collision, as will be described below.

For example, as described above with reference to FIG. 11, in some non-limiting embodiments of the present technology, the processor 550 can be configured to determine, based on the first plurality of vertices 702 and the second plurality of vertices 704, presence of the overlap region 1102 between the first tooth 602 and the second tooth 604 as the first tooth 602 moves along the given segment of its tooth trajectory according to the current orthodontic treatment plan.

Further, in some non-limiting embodiments of the present technology, based on the tooth 3D digital models, the processor 550 can be configured to determine the respective degree of penetration 1104 (for example, in mm) between the first tooth 602 and the second tooth 604 caused by the identified collision as the first tooth 602 moves along the given segment of its tooth trajectory. Thus, in some non-limiting embodiments of the present technology, the processor 550 can further be configured to determine a maximum degree of penetration between the first tooth 602 and the second tooth 604 as the first tooth 602 moves along its respective tooth trajectory, as a whole, according to the current orthodontic treatment plan.

Further, the processor 550 can be configured to determine a collision time interval, during which the first tooth 602 and the second tooth 604 would be colliding as the first tooth 602 moves along the given segment of its tooth trajectory according to the current orthodontic treatment plan.

The method 1400 hence advances to step 1410.

Step 1410: Causing, by the Processor, for the Given Segment of the Current Orthodontic Treatment, Display of Respective Overlap Regions Between the Given Pair of Adjacent Teeth Over an Indication of the Implementation of the Current Orthodontic Treatment Plan Further, at step 1410, the processor 550 can be configured to cause visualization of the so determined collision between the first tooth 602 and the second tooth 604 over the indication implementing the current orthodontic treatment plan, such as in the implementation diagram 1200, as described above with reference with FIG. 12.

More specifically, the processor 550 can be configured to map, to the implementation diagram 1200, values of the collision parameters determined at step 1408, such as the value 1208 of the total maximum degree of penetration between the first tooth 602 and the second tooth 604 and the time interval visual representation 1210 of the collision time interval, as described further above with reference to FIG. 12.

Further, in additional non-limiting embodiments of the present technology, the processor 550 can be configured to take certain preventive actions to resolve the so identified collision between the first tooth 602 and the second tooth 604, thereby generating the updated orthodontic treatment plan, as described above.

More specifically, to resolve the collision between the first tooth 602 and the second tooth 604, in various non-limiting embodiments of the present technology, at a certain stage of the current orthodontic treatment plan prior to the first occurrence of the collision between the teeth the processor 550 can be configured to execute at least one of: (i) re-determining the respective tooth trajectory of at least one of the first tooth 602 and the second tooth 604, as described above; (ii) adding the stripping request for stripping tooth material of at least one of the first tooth 602 and the second tooth 604 sufficient for avoiding the collision without re-determining the tooth trajectories thereof; or (iii) adding the removal request for prescribing removal of at least one of the first tooth 602 and the second tooth 604.

Further, based on the so updated orthodontic treatment plan, the processor 550 can be configured to determine a respective configuration of the aligner 20 to be applied to the upper teeth 16 to cause the first tooth 602 to move towards the target position thereof without causing the collision thereof with the second tooth 604. For example, the processor 550 can be configured to determine configuration of the aligner 20 and further cause manufacture thereof, for example as described in the U.S. Pat. No. 11,191,618-B1 referenced above.

The method 1400 hence terminates.

Thus, certain embodiments of the method 1400 allow identifying and preventing collisions between the subject's teeth in a more efficient manner.

Modifications and improvements to the above-described implementations of the present technology may become apparent to those skilled in the art. The foregoing description is intended to provide certain examples of implementation of the non-limiting embodiments of the present technology and in no way is intended to be limiting. The scope of the present technology is therefore intended to be limited solely by the scope of the appended claims.

The invention claimed is:

1. A method of determining an orthodontic treatment plan for a subject, the method being executable by a processor, the method comprising:
   acquiring, by the processor, a 3D point cloud representative of surfaces of a given pair of adjacent teeth of the subject;
   obtaining, by the processor, an indication of a current orthodontic treatment plan for the subject, the current orthodontic treatment plan including data of respective tooth trajectories for each one of the given pair of adjacent teeth, the respective tooth trajectories being predetermined,
      a given tooth trajectory including a respective plurality of segments defining a path of a respective tooth of the given pair of adjacent teeth from a current position to a target position thereof;
   determining, along a given segment of the respective plurality of segments of at least one of the given pair of adjacent teeth, an occurrence of a collision between the given pair of adjacent teeth, the determining including
      determining if, along the given segment, a first tooth of the given pair of adjacent teeth moves at least one of translationally and rotationally relative to a second tooth of the given pair of adjacent teeth, such that:
         in response to the first tooth moving translationally relative to the second tooth:
            determining, by the processor, based on the 3D point cloud, a reference plane associated with a side surface of the second tooth facing the first tooth;
            determining, by the processor, respective linear distances between each point representative of the first tooth and the reference plane associated with the second tooth; and
            in response to determining at least one respective linear distance exceeding a predetermined linear threshold value, determining the occurrence of the collision between the given pair of the adjacent teeth during implementation of the current orthodontic treatment plan;
         in response to determining that, along the given segment, the first tooth moves rotationally relative to the second tooth:
            determining, by the processor, a distance field associated with the second tooth of the given pair of adjacent teeth;
            determining, by the processor, based on the distance field associated with the second tooth, respective arc distances between each point representative of the first tooth and the surface of the second tooth; and
            in response to determining at least one respective arc distance exceeding a predetermined arc threshold value, determining the occurrence of the collision between the given pair of the adjacent teeth during the implementation of the current orthodontic treatment plan;
   determining, by the processor, a respective overlap region between the given pair of adjacent teeth caused by the collision therebetween along the given segment; and
   causing, by the processor, for the given segment of the current orthodontic treatment, display of respective overlap regions between the given pair of adjacent teeth over an indication of the implementation of the current orthodontic treatment plan.

2. The method of claim 1, further comprising determining the given tooth trajectory for the respective one of the given pair of adjacent teeth based on minimizing, within a predetermined acceptable time range, a time to displace from the current position to the target position.

3. The method of claim 1, wherein prior to the determining any one of the respective linear distances and the respective arc distances, the method comprises:
   generating, by the processor, a voxel grid around the first tooth in the 3D point cloud, a given voxel of the voxel grid includes a respective set of points representative of a surface of the first tooth; and
   determining, by the processor, in the respective set of points, a respective single point for determining one of a respective linear distance and a respective arc distance between the first tooth and the second tooth.

4. The method of claim 3, wherein the determining the respective single point comprises determining, in the respective set of points, an outermost point towards a surface of the second tooth in the 3D point cloud.

5. The method of claim 4, wherein the determining the outermost point comprises applying a Bounding Volume Hierarchy algorithm to the given voxel.

6. The method of claim 1, wherein the determining the reference plane associated with the side surface of the second tooth comprises determining an average plane from a set of points representative of the side surface of the second tooth within the 3D point cloud.

7. The method of claim 1, wherein the determining the reference plane comprises determining a plane extending through at least some outermost points representative of the side surface of the second tooth.

8. The method of claim 1, wherein the determining the occurrence of the collision comprises determining one of a minimum respective linear distance and a minimum respective arc distance exceeding a respective one of the predetermined linear threshold value and predetermined arc threshold value.

9. The method of claim 8, wherein a given one of the minimum respective linear distance and a minimum respective arc distance are determined using a breadth-first search algorithm.

10. The method of claim 1, further comprising updating the current orthodontic treatment plan for resolving the collision between the given pair of the adjacent teeth at the given segment.

11. The method of claim 10, wherein the updating comprises determining a different tooth trajectory for at least one of the given pair of adjacent teeth.

12. The method of claim 10, wherein the updating comprises including, in the current orthodontic treatment plan, a stripping request for stripping material of at least one of the given pair of adjacent teeth within the overlap regions.

13. The method of claim 10, wherein the updating comprises including, in the current orthodontic treatment plan, a removal request for removing at least one of the given pair of adjacent teeth.

14. The method of claim 10, further comprising determining, based on the updated orthodontic treatment plan, a respective configuration of an orthodontic appliance to be applied to subject's teeth over to cause each one of the given pair to displace, along the given segment of the respective plurality of segments, from the current position thereof to the target position thereof without causing the collision therebetween.

15. The method of claim 12, wherein the orthodontic appliance is an aligner.

16. A method of determining an orthodontic treatment plan for a subject, the method being executable by a processor, the method comprising:
   acquiring, by the processor, a 3D point cloud representative of surfaces of a given pair of adjacent teeth of the subject;
   obtaining, by the processor, an indication of a current orthodontic treatment plan for the subject, the current orthodontic treatment plan including data of respective tooth trajectories for each one of the given pair of adjacent teeth, the respective tooth trajectories being predetermined,
      a given tooth trajectory including a respective plurality of segments defining a path of a respective tooth of the given pair of adjacent teeth from a current position to a target position thereof;
   determining, along a given segment of the respective plurality of segments, an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth, such that:
      in response to the first tooth moving translationally relative to the second tooth, applying, by the processor, a first algorithm to determine a plurality of linear distances between each point representative of the first tooth and the second tooth,
         in response to determining at least one of the plurality of linear distances exceeding a predetermined linear threshold value, determining the occurrence of the collision between the given pair of the adjacent teeth
      in response to determining that, along the given segment, the first tooth moves rotationally relative to the second tooth, applying, by the processor, a second algorithm to determine a plurality of arc distances between each point representative of the first tooth and the second tooth,
         in response to determining at least one of the plurality of arc distances exceeding a predetermined arc threshold value, determining the occurrence of the collision between the given pair of the adjacent teeth during the implementation of the current orthodontic treatment plan;
   determining, by the processor, a respective overlap region between the given pair of adjacent teeth caused by the collision therebetween along each one of the respective plurality of segments; and
   causing, by the processor, for each one of the respective plurality of segments of the current orthodontic treatment, display of respective overlap regions between the given pair of adjacent teeth over an indication of the implementation of the current orthodontic treatment plan.

17. A system for determining an orthodontic treatment plan for a subject, the system comprising:
   a processor;
   and a non-transitory computer-readable medium storing instructions;
   the processor, upon executing the instructions, being configured to:
   acquire a 3D point cloud representative of surfaces of a given pair of adjacent teeth of the subject;
   obtain an indication of a current orthodontic treatment plan for a subject, the current orthodontic treatment plan including data of respective tooth trajectories for each one of the given pair of adjacent teeth, the respective tooth trajectories being predetermined,
      a given tooth trajectory including a respective plurality of segments defining a path of a respective tooth of the given pair of adjacent teeth from a current position to a target position thereof;
   determine, along a given segment of the respective plurality of segments, an occurrence of a collision between the given pair of adjacent teeth, the determining including determining if, along the given segment, a first tooth of the given pair of adjacent teeth moves at least one of translationally and rotationally relative to a second tooth of the given pair of adjacent teeth, such that:
      in response to the first tooth moving translationally relative to the second tooth:
         determine, based on the 3D point cloud, a reference plane associated with a side surface of the second tooth facing the first tooth;

determine, respective linear distances between each point representative of the first tooth and the reference plane associated with the second tooth; and in response to determining at least one respective linear distance exceeding a predetermined linear threshold value, determine the occurrence of the collision between the given pair of the adjacent teeth during implementation of the current orthodontic treatment plan;

in response to determining that, along the given segment, the first tooth moves rotationally relative to the second tooth:

determine a distance field associated with the second tooth of the given pair of adjacent teeth;

determining, by the pro determine, based on the distance field associated with the second tooth, respective arc distances between each point representative of the first tooth and the surface of the second tooth; and in response to determining at least one respective arc distance exceeding a predetermined arc threshold value, determine the occurrence of the collision between the given pair of the adjacent teeth during the implementation of the current orthodontic treatment plan;

determine, a respective overlap region between the given pair of adjacent teeth caused by the collision therebetween along each one of the respective plurality of segments; and cause, for each one of the respective plurality of segments of the current orthodontic treatment, display of respective overlap regions between the given pair of adjacent teeth over an indication of the implementation of the current orthodontic treatment plan.

18. The system of claim 17, wherein prior to the determining any one of the respective linear distances and the respective arc distances, the processor is configured to:

generate a voxel grid around the first tooth in the 3D point cloud, a given voxel of the voxel grid includes a respective set of points representative of a surface of the first tooth; and determine, in the respective set of points, a respective single point for determining one of a respective linear distance and a respective arc distance between the first tooth and the second tooth.

19. The system of claim 18, wherein to determine the respective single point, the processor is configured to determine, in the respective set of points, an outermost point towards a surface of the second tooth in the 3D point cloud.

20. The system of claim 17, wherein the processor is further configured to update the current orthodontic treatment plan for resolving the collision between the given pair of the adjacent teeth at each treatment interval.

\* \* \* \* \*